(12) United States Patent
Shofner, II et al.

(10) Patent No.: US 6,854,460 B1
(45) Date of Patent: Feb. 15, 2005

(54) CONTROLLED DELIVERIES AND DEPOSITIONS OF PHARMACEUTICAL AND OTHER AEROSOLIZED MASSES

(75) Inventors: F. Michael Shofner, II, Knoxville, TN (US); Frederick M. Shofner, Knoxville, TN (US)

(73) Assignee: Shofner Engineering Associates, Inc., Knoxville, TN (US)

( * ) Notice: Subject to any disclaimer, the term of this patent is extended or adjusted under 35 U.S.C. 154(b) by 0 days.

(21) Appl. No.: 09/937,584

(22) PCT Filed: Mar. 30, 2000

(86) PCT No.: PCT/US00/08354

§ 371 (c)(1),
(2), (4) Date: Sep. 26, 2001

(87) PCT Pub. No.: WO00/58016

PCT Pub. Date: Oct. 5, 2000

Related U.S. Application Data

(60) Provisional application No. 60/143,732, filed on Jul. 14, 1999, and provisional application No. 60/127,219, filed on Mar. 31, 1999.

(51) Int. Cl.$^7$ .............................................. B65D 83/06
(52) U.S. Cl. .............................. 128/203.15; 128/203.12
(58) Field of Search ....................... 128/200.14–200.24, 128/203.12, 204.18, 203.15, 203.21

(56) References Cited

U.S. PATENT DOCUMENTS

| | | | |
|---|---|---|---|
| 4,029,482 A | * | 6/1977 | Postma et al. .................... 55/2 |
| 4,184,258 A | | 1/1980 | Barrington et al. |
| 4,634,459 A | * | 1/1987 | Pischinger et al. ............ 55/418 |
| 4,801,411 A | * | 1/1989 | Wellinghoff et al. ............ 264/7 |
| 4,872,786 A | | 10/1989 | Braden |
| 5,248,448 A | | 9/1993 | Waldron et al. |
| 5,263,475 A | | 11/1993 | Altermatt et al. |
| 5,349,947 A | | 9/1994 | Newhouse et al. |
| 5,388,574 A | | 2/1995 | Ingebrethsen |
| 5,542,412 A | | 8/1996 | Century |
| 5,567,472 A | | 10/1996 | Siegfried et al. |
| 5,829,434 A | | 11/1998 | Ambrosio et al. |
| 6,010,038 A | | 1/2000 | Dietrich |
| 6,221,136 B1 | * | 4/2001 | Liu et al. ....................... 96/66 |
| 6,234,169 B1 | | 5/2001 | Bulbrook et al. |

FOREIGN PATENT DOCUMENTS

| | | |
|---|---|---|
| DE | 195 00 726 A1 | 7/1996 |
| EP | 0789230 A1 | 8/1997 |
| EP | 0826386 A2 | 3/1998 |
| EP | 0864849 A1 | 9/1998 |

* cited by examiner

*Primary Examiner*—Glenn K. Dawson
(74) *Attorney, Agent, or Firm*—Carter Schnedler & Monteith, P.A.

(57) ABSTRACT

A system (1) for the precisely and accurately controlled delivery and collection of aerosolized masses. The system (1) includes an aerosol generator (100), an upstream electro-optional aerosol mass concentration sensor (200) past which aerosols are transported at a known upstream volumetric flow rate, a deposition zone (300) within which aerosols are collected on or within a media, and a downstream electro-optical aerosol mass concentration sensor (201) past which aerosols uncollected in the deposition zone (300) are transported at a known downstream volumetric flow rate. The net mass of aerosols collected in the deposition zone (300) is determined by integrating over time the product of mass concentration measured by the upstream electro-optical sensor (200) and the upstream volumetric flow rate minus the product of mass concentration measured by the downstream electro-optical sensor (201) and the downstream volumetric flow rate. The aerosol generator (100) includes a metering pocket into which powder is loaded, and a fluidizing jet which produces an expansive bolus that is directed into a mixing chamber. The deposition zone (300) collects aerosols by filtration, impaction or electrostatic attraction.

20 Claims, 15 Drawing Sheets

CONTROLLED DELIVERIES AND DEPOSITIONS OF PHARMACEUTICAL AND OTHER AEROSOLIZED MASSES

CROSS-REFERENCE TO PROVISIONAL PATENT APPLICATIONS

The benefit of U.S. Provisional Patent Application Ser. No. 60/127,269, filed Mar. 31, 1999; and 60/143,732, filed Jul. 14, 1999, is claimed.

TECHNICAL FIELD

This invention relates to controlled deliveries of aerosolized masses, such as the delivery of small aerosolized masses of active pharmaceuticals to deposition zones onto much larger inert carriers, or delivery of large mass flows to combustion zones. Illustrative fields of utility are pharmaceutical manufacture, clinical or patient-administered respiratory therapy, powder coatings Mi of materials, food-stuffs manufacture, such as coffee, confections, freeze-dried powder packaging, printing systems, powdered coal or atomized fuel oil for electric power generation, and the like. The range of precisely and accurately delivered mass flow rates may range from nanograms per second to pharmaceutical deposition zones to tonnes per hour to combustion zones of a coal-fired power plant.

BACKGROUND ART

Because the preferred embodiments disclosed below are primarily directed to applications within the field of pharmaceutical manufacture, the background and needs addressed in that field are discussed below in relatively greater detail, with a few brief comments directed to the other fields of use. The delivery of pharmaceutical chemicals, or medications, or "medicaments" for therapeutic purposes is currently accomplished by ingesting a "pill" to be taken into the digestive tract, by breathing aerosolized liquids or powders for intake into the respiratory tract, and by direct injection or by transdermal diffusion into the circulatory system of mammals. In many current applications of these delivery methods, the bioactive component is a small, of the order of about lot, of the total delivery of active and inert material. The larger portion is a more or less inert material such as starch powders in the case of pill delivery, water or alcohol, or a mixture thereof, for inhalation delivery, or saline solution for injection or transdermal delivery. As a common example, in a pill which is formed by mixing active and inert powders, the active dose may have mass of 10 milligrams and the inert carrier may have mass of 100 milligrams, with the resulting active/inert mass ratio of the order of 10:100 or 10%.

It will be appreciated that known formulation or mixing technologies make it difficult to achieve good precision and accuracy even when the dose is about 10 mg and the active/inert fraction is about 10%. Prior art technologies limit the precision in the delivery, pill-by-pill, of the active medicament, to about 15%. Batch-to-batch absolute accuracies of about 10% are typical of current art. (As employed herein, precision means standard deviation divided by the mean of individual dosages within a batch. As employed herein, accuracy means the degree to which the average and absolute dosage of each batch agrees with the prescribed value.) Since these precisions and accuracies become even worse as the ratio of active to inert components falls, it follows that prior art mixing is severely limiting progress and dramatic improvements are needed. These limitations of prior art deliveries, to high active/inert fractions and high dosages, are thus in conflict with two of the much-desired features of modern pharmacology: decreasing active/inert fractions and decreasing active dose size. It can be appreciated that what matters, for proper therapeutic treatment, is the precision and absolute accuracy in the delivery of the active component, and of its bioavailability. The precision and accuracy in delivery of the inert carrier do not matter, as much. It can be further appreciated that the prior art precisions and accuracies are discomfortingly problematical, even for today's relatively high dosage levels and high active/inert fractions. Some pharmaceuticals are potentially harmful in even slight overdoses. On the other hand, underdosing will not produce the desired therapeutic results. Using the 15% precision and 10% accuracy values given above, the worst-case combinations of pill-to-pill precisions and batch-to-batch accuracies statistically allow, with disconcerting frequency, more than ±25% dosage variabilities with respect to the dosage prescribed by the physician, and expected by the patient. It follows that the variabilities in dosage deliveries associated with prior art apparatus and methods are only marginally acceptable now, with high dose levels and high active/inert fractions, and are increasingly unacceptable as the level or fraction decrease, and are thereby limiting progress.

DISCLOSURE OF THE INVENTION

Accordingly, a primary need addressed by the invention is to improve the precision and accuracy of aerosolized masses delivered to deposition zones or collection sites. Thus, the invention is embodied in aerosol generators, and there are embodiments which include aerosol mass flow measurement. Another need addressed is for improved collection, particularly for pharmaceutical manufacture, and especially when small and very small doses of active medications, milligrams to nanograms, are collected on or in inert carrier materials for ingestion, inhalation and injection or transdermal deliveries. A still further need addressed is to provide improved precision and accuracy for low and very low active/inert mass fractions. In an exemplary embodiment, a system for delivery and deposition of aerosolized masses includes an aerosol generator. Following the aerosol generator is an upstream electro-optical mass concentration sensor, and a source of gas flow for transporting aerosols past the upstream electro-optical mass concentration sensor at a known upstream volumetric flow rate, in turn followed by a deposition zone for collecting aerosols on or within a media. Downstream of the deposition zone is a downstream electro-optical mass concentration sensor for measuring the mass concentration of aerosols uncollected in the deposition zone, and a conduit for transporting uncollected aerosols past the downstream electro-optical mass concentration sensor at a known downstream volumetric flow rate. A controller is connected to the upstream and downstream mass concentration sensors and determines the net mass of aerosols collected within the deposition zone by integrating over time the product of mass concentration measured by the upstream electro-optical sensor and the known upstream volumetric flow rate minus the product of mass concentration measured by the downstream electro-4: optical sensor and the known downstream volumetric flow rate. An exemplary embodiment of an aerosol generator for producing an aerosolized powder includes a metering pocket, and powder is loaded into the metering pocket. A jet directs high velocity gas into the metering pocket so as to fluidize the powder and produces an expansive bolus. The expansive bolus is directed into a mixing chamber. Another exemplary embodiment of an aerosol generator includes a source of a liquid solution of an active ingredient and a volatile solvent, an atomizer for atomizing the solution to produce droplets from which the solvent evaporates to leave an expansive bolus of solute residue, and a mixing chamber into which the expansive bolus is directed. An exemplary embodiment of a deposition zone for collecting aerosolized masses includes a porous media collection element, an aerosol delivery tube positioned generally against an upstream side of the porous media collection element for delivering aerosols transported by a fluid, and a perforated support element positioned generally against a downstream side of the porous media collection element. Another exemplary embodiment of a deposition zone for collecting aerosolized masses includes an impactor plate, an impactor jet for directing aerosols transported by a fluid against the impactor plate for deposition thereon, and an output conduit for conveying away fluid and aerosols not deposited on the impactor plate. Yet another exemplary embodiment of a deposition zone for collecting aerosolized masses includes a mass delivery section for loading an aerosolized mass into a removable drift tube, and a deposition section receiving the drift tube and including a source of displacement gas for directing the aerosolized mass over a deposition surface.

BEST MODES FOR CARRYING OUT THE INVENTION

Figure 1:
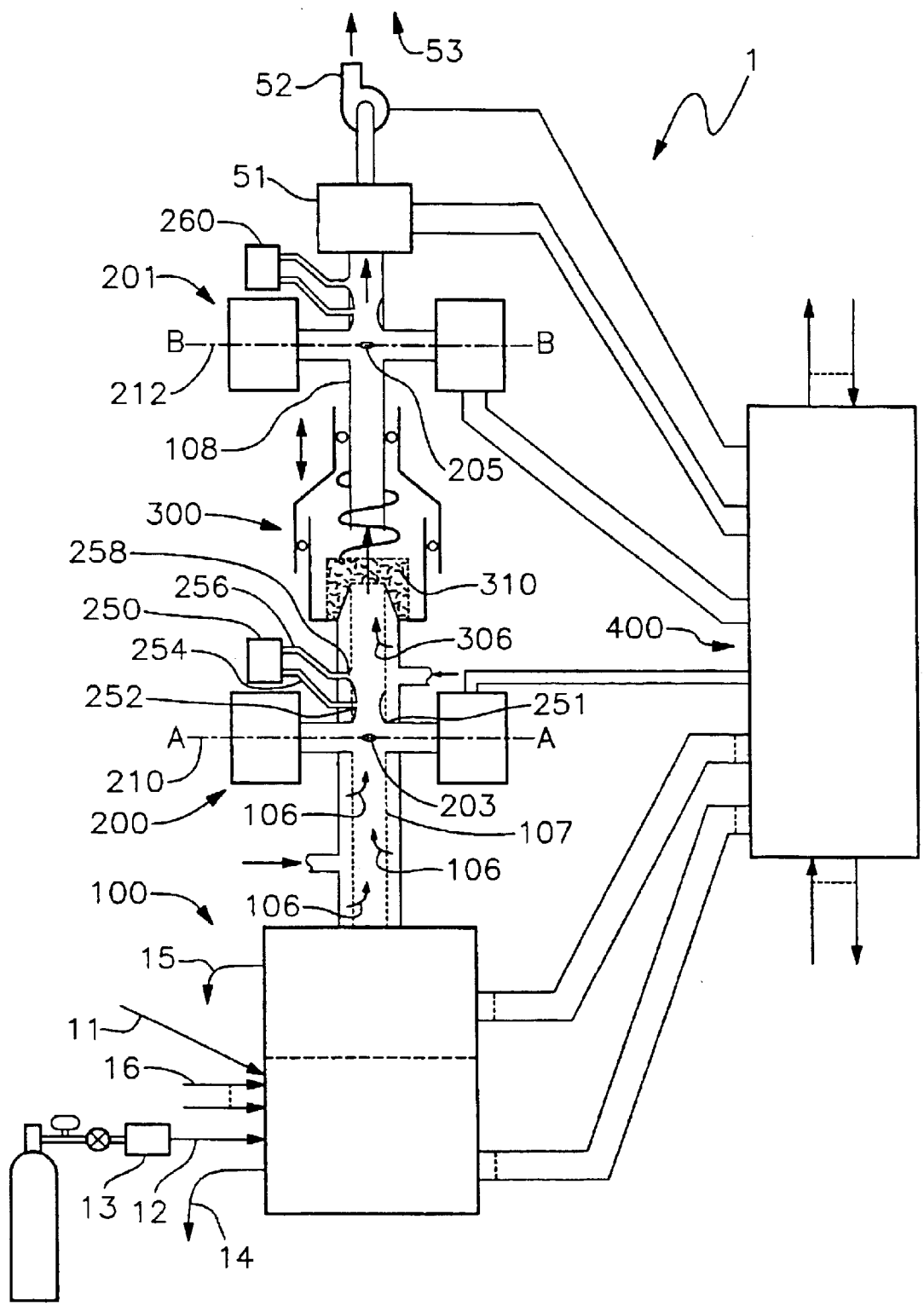
FIG. 1 is a schematic depiction of a system embodying the invention.

Embodiments of the invention provide methods and apparatus for aerosol generation and for deposition which are optimally combined with aerosolized mass flow rate or mass deliveries. In very brief summary, aerosol generator embodiments utilize impulsive or continuous injection of "expansive boli" into mixing/stilling/classification chambers, which we refer to as mixing chambers. Collection media embodiments use the principles of filtration by porous, inert powders; impaction; and electrostatic attraction. Aerosolized mass flows from the aerosol generators are measured by electro-optical sensors and the mass flow deliveries to the deposition zones are controlled by associated control electronics. In our developments of rigorous mass flow sensors, we determined that the most general and basic case requires measurement of the number of aerosolized particles per second transported across a differential element of the cross sectional area of a conduit and the mass per particle. Summation or integration yields aerosol mass flow rate, dM/dt, in grams/second flowing in the conduit, normal to and across the cross section. Summation or integration over all particle sizes yields total mass flow rate, and summation or integration over time yields mass delivery in time T. Significantly, dM/dt so measured is dependent only on aerosol properties, including their spatial and vector velocity distributions, and not on gas properties. Surprisingly, we discovered that, in some special but practical cases, a "scalar" formulation and measurement permits sufficient precision and accuracy. We determined that such is valid when the aerosol sizes and speeds are small, when their vector directions are substantially parallel to the conduit, and when all particle sizes or classes are moving at nearly the same velocity as the mean transporting fluid velocity. We experimentally determined that this discovery is generally valid for aerosol sizes up to 20 gm, speeds up to 1 m/s, conduit internal diameters of order 1 cm, and transporting gases of air or nitrogen roughly near standard temperatures and pressures. We also determined conditions for which these generalities may be relaxed or restricted. In these special conditions, the aforementioned "scalar" mass flow measurement, dM/dt, in grams/sec moving across a cross sectional plane of the conduit, is effected by independently measuring the volumetric gas flow rate Q, $m^3$/sec, and aerosol mass concentration C, grams/$m^3$. Embodiments of our invention achieve practical and combined realization of the foregoing, especially including accuracy and precision of mass flow deliveries of about 5% and which can, in some cases, approach the order of It. There are no fundamental limits for our methods to dosage size or active/inert mass fractions. Dose deliveries that are as small as 1 microgram of active medication, with extension upward to milligrams and higher and downward to nanograms and lower are provided. These improved precision and accuracy results are achieved in spite of smaller and smaller ratios of active to inert components, versus order of magnitude 10% for prior art. Importantly, there are under evaluation powerful, expensive, new drugs, where the bioactive dose is only a few micrograms. When carried by an inert material whose mass is a few hundred milligrams, the mass ratio of active medication to inert carrier is evidently of the order of 1:100,000 or 0.001%. Another important medical application of the invention is in the field of respiratory therapy, wherein improved dosage precision and accuracy enable better treatments and quantitative evidence therefor, in clinical settings. Still another health science application of our invention is to provide for improved apparatus and methods for administering direct therapeutic delivery of medication within the clinical setting of a hospital, physician's office, pharmacy, assisted living facility, veterinary clinic, and the like, thus providing the option for a physician or health care worker to administer precise and controlled delivery of medicaments to a patient where __20 supervision or eminent need is required, and for which definitive documentation of delivered dose is important or required. To further illustrate the breadth of applicability of the invention, the invention may be embodied in improved apparatus and methods for controlled deliveries of powderized coal or atomized fuel oil, thus optimizing combustion efficiencies thereof, as well as reducing emissions from power plants. The invention may be embodied in improved apparatus and methods for bulk powder deliveries in the manufacturing and packaging industry. For example, particle size of coffee is critical to the solubility of the grinds and therefore, brew strength and taste performance. As employed herein, "aerosol" is a generic term which refers to finely divided liquid and dry powder materials, such as "atomized" sprays and "fluidized and dispersed" powders, respectively. To "aerosolize" a bulk liquid or powder generally means to break up the bulk material into small particles and to disperse them into a fluid medium, usually gaseous, for transport. Aerosolization is a key component of the aerosol generation and transport aspects of our invention and is explained in detail hereinbelow. The sizes of such finely divided particulate materials are in the range of less than about 1 micrometer, gm, to several hundred Am in diameter. For reference purposes, respirable therapeutic aerosols are preferably of the order of a few Am, or smaller than about 10 Am, in order to reach the deep, alveolar recesses of the lungs. The therapeutic aerosol size range is between 10 Am and 100 gm for collection by or deposition within the bronchia, and the size range is greater than 100 Am for nasal collection. "[1]Respirable aerosols" are defined by the US Occupational Safety and Health Administration (OSHA) and Environmental Protection Agency (EPA) to be below about 10 Am; these governmental agencies indeed enforce laws which regulate the concentrations of so-called Particulate Matter-10 gm (PM 10 Standard) or corresponding definitions of aerosol size to which US citizens and workers are exposed in the ambient environment and in the workplace, respectively. For oral injection or transdermal deliveries, aerosol size ranges are also typically 1-10 Am.

1. Mass Delivery Measurements and Controls

Known aerosol mass concentration measurement methods typically employ electro-optical, light scattering means. Sensors have been developed and sold by ppm, Inc., of Knoxyille, Tennessee, which sensors measure mass concentration C, $g/m^3$, over the range of less than 1 $Ag/m^3$ to over 100 $g/m^3$. (Note: $g/m^3$=grams of mass per cubic meter of volume.) Aerosols measured have been suspended in or transported by all types or compositions of gases, at pressures ranging from tens of atmospheres down to hard vacuums, and over wide temperature ranges. The compositions and sizes of the particles have covered most types imaginable, from those affecting semiconductor manufacturing to respiratory health to explosive dusts. Particle sizes have ranged from less than 1 pm to over 1000 Am in diameter. A major feature of one of our methods is the ability to produce particle sizing information in the form of mass fractions. Our measurements of mass concentration are mass per unit volume of space, without reference to the pressure, temperature, or composition of the transporting gas flow. We have discovered that mass delivery rates, dM/dt, g/sec, can be measured and precisely and accurately controlled, using adaptations and improvements of existing methods for measuring mass concentrations C, $g/m^3$, in combination with known measurements of volumetric flow rates Q, $m^3/sec$. FIG. 1, which is partly block and partly unscaled schematic in format, illustrates an exemplary embodiment in the form of a system 1 for the precisely and accurately controlled delivery of aerosolized masses, and for their collection.

System 1 in overview comprises four subsystems: aerosol generator (AG) 100, upstream and downstream electro-optical (EO) mass concentration aerosol sensors 200 and 201, collection surface or volume or deposition zone (DZ) 300, and control and communications module (CCM) 400. Disclosed in detail below are the first three of the major subsystems of this pharmaceutical manufacturing embodiment of our controlled mass delivery and collection system 1. We note preliminarily the delivery or loading of bulk powders or liquids 11 into the aerosol generator 100, the provision of aerosolizing and transport gas or liquids 12 and contamination protection filters 13, and the discharge from aerosol generator 100 of "waste streams" of raw aerosol material 14 or aerosolizing and transport fluids iS. These latter discharges may be of aerosols which are incorrect in size or some other physical or chemical attribute, and thus rejected from the aerosol generator 100, or unused fluids associated therewith. Also to be noted are the provision of such utilities as electrical power, compressed gases, or cooling/heating liquids and the like 16, all of which are well known and generally not shown for clarity of illustration. Particular attention is now drawn to plane AA 210, across which plane aerosols having mass concentration C are transported by gas flow Q in perforated transport tube or conduit 107. The average aerosol mass concentration C is measured in or near this plane AA 210 by upstream electro-optical mass concentration sensor 200. The aerosols are subsequently to be collected or deposited in deposition zone 300. The particular deposition medium 310 shown in FIG. 1 as an example is porous, inert powder, described in greater detail hereinbelow with reference to FIG. 4A. However, the deposition zone 300 may be embodied in a number of different ways, for example as are described hereinbelow with reference to FIGS. 4B, 4C, 4D, 4E and 4F. The aerosols are transported across plane AA 210 with essentially uniform average velocity by gas having a volumetric flow rate of Q, $m^3/sec$. We discovered that the aerosol mass delivery rate across plane AA 210 obeys, in a simple scalar but useful approximation:

$$M = dM/dt = Q \times C \text{ (grams/sec)} \quad (1)$$

and the aerosol mass delivered or transported across plane A 210 in time interval (0, T) is thus $$M = \int_0^T QC\,dt. \quad (2)$$

In the general case, and most definitely in the case of those embodiments where aerosolization is pulsed in nature, thus leading to varying mass concentrations C and flow rates Q from aerosol generator 100, the integral of Equation (2) is solved with appropriately small time increments to precisely and accurately control the mass delivered. This is accomplished with the control and communication module CCM 400. For purposes of explanation, it may be assumed that Q and C are steady, or constant in time, in which case the integral equation solution is trivial and the transported mass is simply $$M = QCT \text{ (grams)}. \quad (3)$$

As a numerical example, representative values of
Q=1 liter/min=16.7 ml/sec=$16.7 \times 10^{-6}$ $m^3/sec$
C=1 $g/m^3$=1000 $\mu g$/liter, and
T=1 sec
yields $$M = 16.7 \, \mu g. \quad (4)$$

That is, 16.7 μg of mass is transported within tube 107 in each second across plane AA 210 when the average flow rate Q=1 liter/min and the Concentration C=1 g/m³. These calculations reasonably illustrate the orders of magnitude for pharmaceutical manufacturing.

Different embodiments of the invention operate at very different values of QCT. Nanograms of mass delivery correspond to lower values of QCT, and tonnes of delivery correspond to higher values of QCT, but the principles are the same.

For purposes of accuracy and precision and on-line quality assurance, as explained below, especially when the aerosol deposition efficiency at deposition zone 300 is less than 100%, a similar measurement and calculation apply at plane BB 212, which is downstream of the deposition zone 300. Uncollected aerosols are transported within conduit 108 across plane BB 212, and measured by downstream mass concentration sensor 201. The volumetric flows Q are not necessarily the same at plane BB 212 as at plane AA 210; they differ primarily by sheath or purge flows 306 introduced downstream of sensor 200. (Sheath flow 106 is included in Q in the above calculation.) In some embodiments, perforated transport tube 107 is made solid and the purge/sheath introduced elsewhere or not at all.

It will again be appreciated that a more general and fundamental formulation of Equation (1) is required for more complex instrumental measurements and apparatus. A vector formulation must be used if the aerosols are not being transported at the same vector velocities as those of the transport fluid, which fluid may be gas or liquid, or if the transport flux varies significantly over the cross-sections. We discovered that the assumptions enabling the scalar calculations and simpler measurement systems for Q and C and formulation dM/dt=QC are frequently valid and of important practical applicability to many of the uses of the invention. This practical applicability is especially valid for pharmaceutical manufacturing where the aerosols are "respirable" in size, i.e., below about 10 micrometers in diameter, and moving at velocities typically below 1 meter/sec within conduits of internal diameter of order centimeters.

The upstream and downstream electro-optical mass concentration sensors 200 and 201 for C, as well as upstream and downstream volumetric flow rate sensors 250 and 260 for flow Q, operate at localized points within the transport tubes or conduits 107 and 108. It follows that these points must be representative of the total transporting cross section. Upstream and downstream volumetric gas flow rate Q sensors 250 and 260 in FIG. 1 are physically near the measurement zones 203 and 205 of respective upstream and downstream mass concentration C sensors 200 and 201. In the embodiment of FIG. 1 the upstream and downstream volumetric gas flow sensors 250 and 260 are venturi flow sensors operating as follows: sensor 250 senses differential pressure developed between throat tap 252 and wall tap 258, which taps are connected to differential pressure sensor 250 by tubes 254 and 256. This differential pressure reading is related to the volumetric flow rate Q flowing into venturi inlet 251 which is physically very near upstream mass concentration sensor measurement zone 203. Accordingly, in this manner C and Q are measured at the same thermodynamic and fluidynamic conditions. Elements and function of downstream volumetric flow sensor 260 are identical. Whereas it is important that C and Q correspond to the same conditions, in some embodiments volumetric flow rate Q is measured elsewhere in the system, but the readings are always adjusted to correspond to the conditions at the location of the mass concentration C sensors.

Whereas most of the drawing in FIG. 1 is block in format, collection surface or volume in deposition zone DZ 300 is shown schematically but without scale to more clearly describe its function in the aerosol mass delivery and collection system 1. Simply stated, the purpose of that part of the system prior to plane AA 210 is to precisely and accurately control the delivery of the aerosol mass which is transported across plane A 210 and then, presumably without significant loss or gain, delivered finally to collection surfaces or volumes 310 in deposition zone 300. The purpose of that part of the system downstream of deposition zone 300 is to assure that all, or at least a measured amount or fraction, of the mass reaching collector 310 is retained thereby, by measuring the uncollected mass with sensor 201, and then to filter 51 the fluid flow 50 prior to entrance into downstream pump 52 and into the environment 53.

In this embodiment, the uncollected aerosol mass reaching transport plane BB 212 is determined based on measurements by downstream mass concentration sensor 201 and downstream volumetric flow rate sensor 260, and this mass is subtracted from that crossing plane AA 210. Mass conservation or mass balance yields the net mass $M_n$ actually retained by collector 400, again assuming no loss or gain of mass elsewhere:

$$M_n = \int_0^T (Q_a C_a - Q_b C_b)\, dt. \tag{5}$$

The a and b subscripts refer to planes AA and BB. Validity of the assumption that the difference is just the mass deposited is verified operationally, and leads to on-going calibration corrections for wall losses or gains or small shifts in sensor calibrations. Wall losses are minimized by introduction of sheath gas flows 106 and 306.

Electro-optical sensors 200 and 201 which are satisfactory for most applications are well known and are manufactured as standard products by ppm, Inc., of Knoxville, Tenn. The series of standard sensor known as "TX," originally developed for inhalation toxicology work, with its associated electronics, has been found to be entirely satisfactory in embodiments of the invention, especially with its mass traction capabilities.

2. Aerosol Generators

Described next are details of four embodiments of aerosol generator (100). In general, these embodiments have the following common features or elements: high velocity, approaching Mach 1, aerosolizing jets; small, of order 1 mm³ "pockets" or fluid elements; impulsive or continuous, or both, expansive boli; delivery of the expansive boli into mixing, stilling, and classifying chambers; and delivery from the mixing chambers of the so-aerosolized mass for subsequent measurement and deposition. (Known prior art aerosol generators have been used for calibrating electro-optical or other aerosol sensors, for supplying aerosols for control equipment testing, and for toxicology studies, usually with animals, and are available from ppm, Knoxville TN or TSI, St. Paul, MN. They lack elements of the subject invention and have not been and cannot be used for precisely and accurately controlled mass deliveries.)

A. Microscoop

Figure 2:
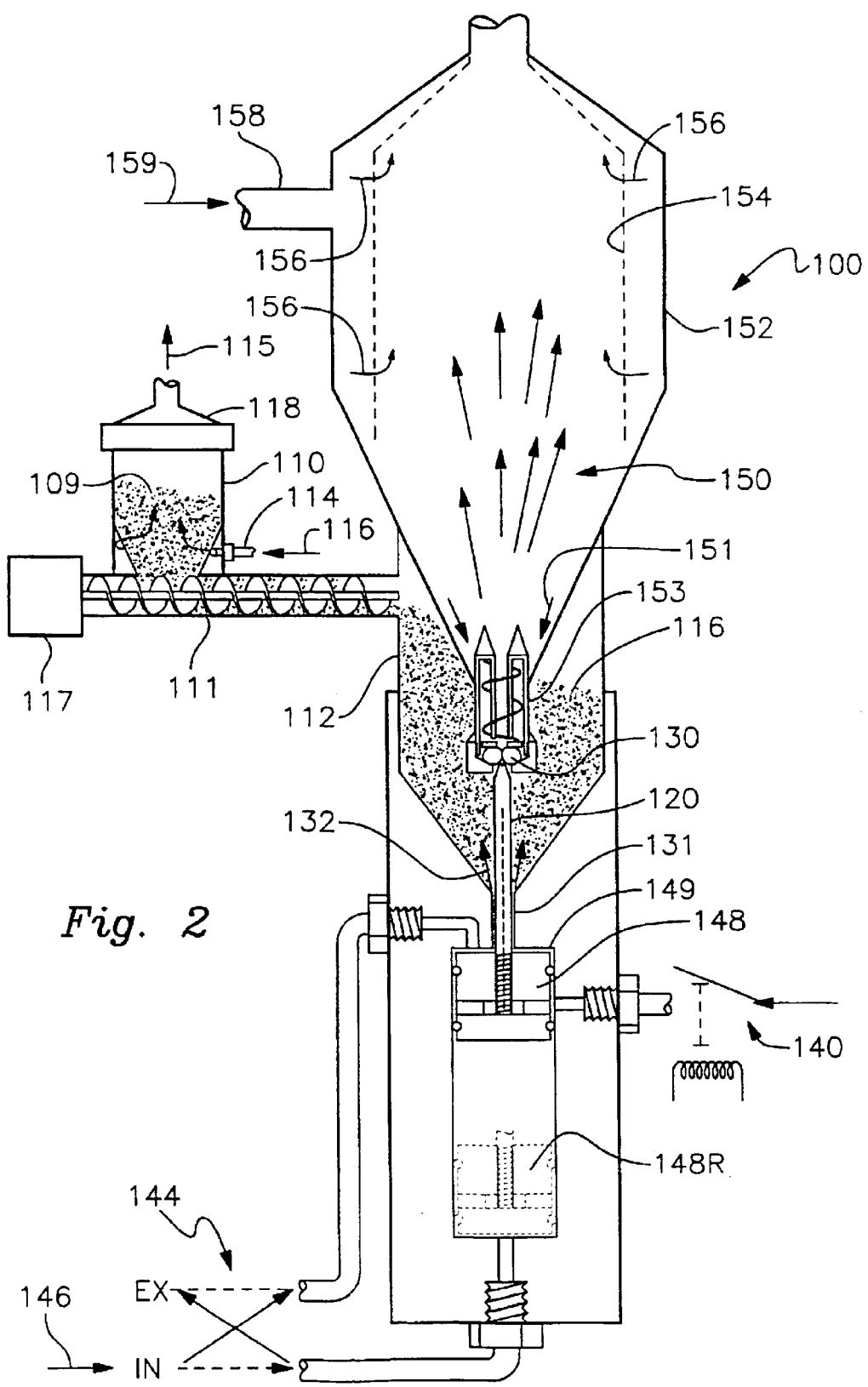
FIG. 2 shows an aerosol generator embodying the invention.

FIG. 2 discloses a first embodiment for aerosol generator 100 herein referred to as a "Microscoop," that is compatible with the rest of controlled mass delivery/deposition system 1 of FIG. 1. In FIG. 2, bulk powder 109 is introduced into supply and preconditioning chamber 110 and is then transferred to aerosol generator powder chamber 112 by auger 111 or other mechanical device. Supply and preconditioning chamber 110 is sealed except for provisions to receive 114 and discharge 115 preconditioning gas 116. A suitable sensor (not shown) and motor 117 drive maintain in the aerosol generator powder chamber 112 a proper level of powder to be aerosolized 116. Other sensors (not shown) are provided to alert the operator when the supply powder level is low in supply and preconditioning chamber 110.

Figure 3:
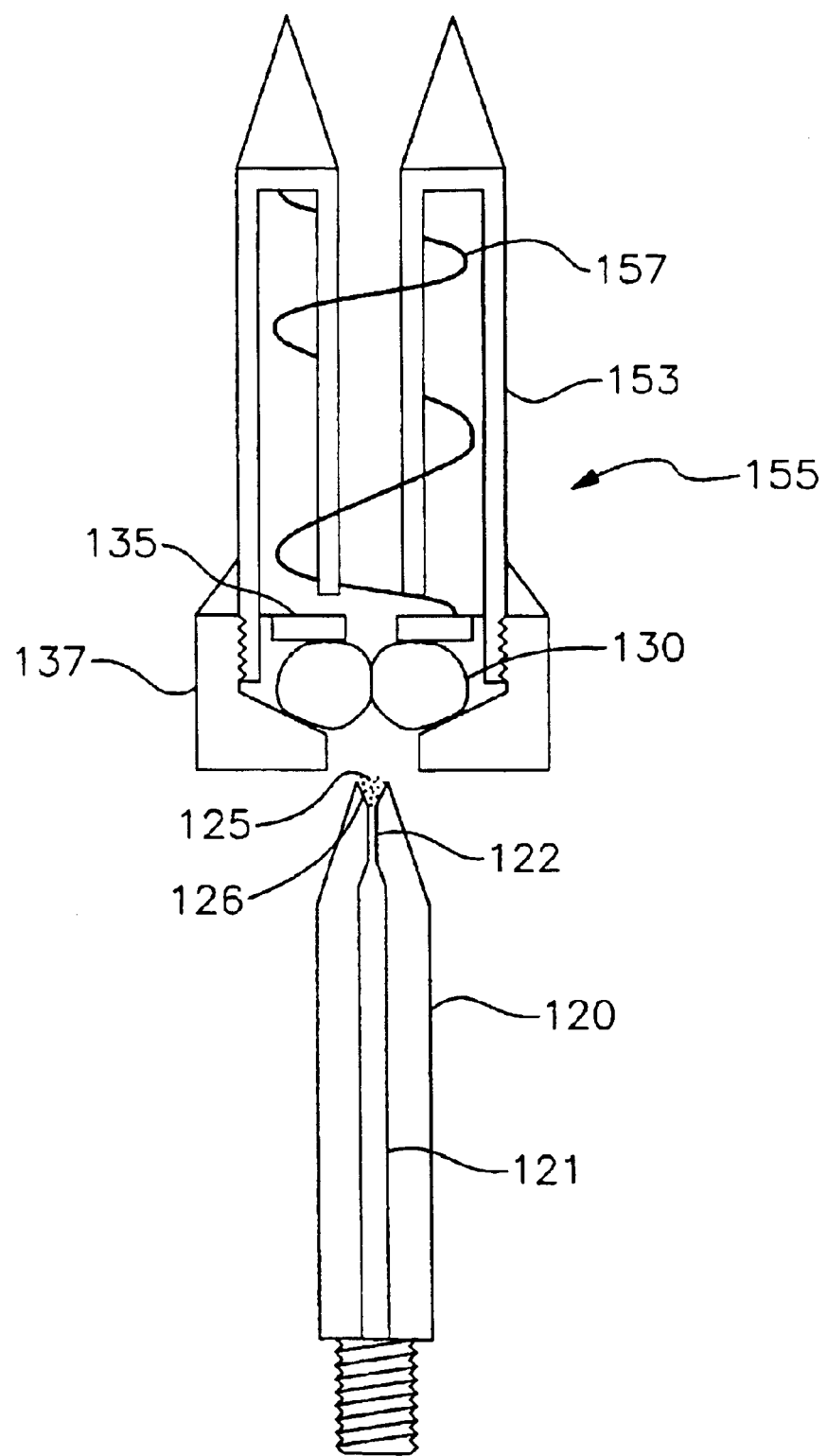
FIG. 3 is an enlarged view of a microscoop plunger.

An important element of aerosol generator 100 is a "microscoop" or plunger rod 120, shown in its extended position in FIG. 2 and in enlarged detail in FIG. 3. At the tip of plunger rod 120 is a pocket 126, having a volume of order 1 mm$^3$ or smaller. Microscoop 120 and sealing gland 130 are described in greater detail hereinbelow with particular reference to FIG. 3. In the extended position of FIG. 2, the plunger rod 120 engages and penetrates elastomer sealing gland 130 and, upon doing so, the powder "scooped" up in the pocket or tip 126 of plunger rod 120 is aerosolized by application of a high velocity jet into pocket 126 through orifice 121. This jet may be continuous or impulsive or both. For impulsive operation a high-pressure gas pulse is applied via solenoid valve 140 and the gas flows through coupling conduit 121 to orifice 122.

We have found it particularly advantageous to operate the orifice 122 at critical pressure ratio wherein the jet velocity approaches Mach 1. This small, high velocity, and highly turbulent jet emanating from orifice 122 into pocket 126 very effectively aerosolizes powder 125. By "aerosolize" we mean that powder 125 is fluidized and transported from pocket 126 into expansive bolus 150 and thence into mixing chamber 152.

Microscoop 120 is rigidly secured to piston 148. Solenoid valve 144 provides compressed gas, delivered at the "In" port 146, which drives piston 148. When solenoid valve 144 is energized, piston 148 is driven from its retracted position 148R (shown dashed in FIG. 2) from the lower end of the bore 150 and intentionally "crashes" into age the upper end of the bore 149, thus inducing vibratory action on powder 116 in chamber 112. The intensity of the "crash" is controlled by pneumatic damping and/or elastomer washers between the top of piston 148 and the upper end of the cylinder bore 149. The vibratory motion causes the powder 116 to feed downward and to cover microscoop 130 when it is in its retracted position 148R, which occurs when piston 148 is driven to the bottom of the bore 150 and also controllably "crashes."

Powder 116 is kept out of the annulus between microscoop plunger rod 120 and the guide hole 131 by causing gas to be driven into the annulus, where it escapes into powder chamber 112, as illustrated by gas flow arrows 132. This gas flow may also be used to condition powder 116 and is vented via the auger 111 and out through supply chamber cap 118, combining with conditioning flow 116 and discharging collectively at 115. Referring to FIG. 3, the powder "scooped-up" by microscoop pocket 126 is impulsively aerosolized by a high pressure, short duration gas pulse, applied at the "In" port of solenoid valve 140 (FIG. 2). The gas pressure is about 10 bar and the pulse duration is about 10 milliseconds. Continuous aerosolization may also be used for powders that are easier to deagglomerate and disperse. Electrical interlocks (not shown) ensure that solenoid valve 140 can only be energized when piston 148 is at the top of its stroke, in the extended position.

The aerosolizing gas pulse is introduced through the center of microscoop rod 120, which is a drilled hole 121 preferably of about 1.0 mm. The hole or orifice 122 at the tip of microscoop 120 is much smaller, about 0.25 mm; the hole or orifice 122 in FIG. 3 is at the bottom of microscoop pocket 126, but it may enter elsewhere, such as through the side of pocket 126. Multiple entries into pocket 126 may be used.

The aerosolized powder and expanding, aerosolizing gas produces an "expansive bolus" 150 in FIG. 2 which energetically enters mixing, stilling and classification chamber 152, and disperses throughout. Sheath gas 159, introduced at inlet 158, and flowing though perforated walls 154, in combination with the aerosolizing gas from microscoop 120, transports the aerosolized particles to the downstream parts of the system 1. Purposes of the gas flowing through the perforated walls 154 are to minimize wall deposition losses, in addition to transporting the aerosolized particles with expansive bolus 150 further into the system. In some applications, the perforated wall flows are unnecessary and the transporting gases are introduced elsewhere or not used at all. This is the case for easily aerosolized powders or whenever continuous aerosolizing and transport flows are used.

Particles which do not deagglomerate as a consequence of the aerosolization prior to and within the expansive bolus 150, or which reagglomerate, and thus are too large to ascend the tube 154, settle or "elutriate" out of the mixing chamber 152 and eventually fall back into the powder chamber 112, as indicated by settling arrows 151. An example of such classification is given later.

The nonbiased sampling feature of microscoop 120 sampling of bulk powder 153 is an important aspect of this embodiment of the invention. Utilization of most of the supply powder is another important feature.

Referring in particular to FIG. 3, microscoop plunger 120 is shown just prior to engaging elastomer gland 130. Also shown are the compressed gas delivery hole 121, the aerosolizing orifice 122 and the concave microscoop pocket 126 holding its catch of powder 125 to be aerosolized. Sealing by elastomer 130 permits the mixing chamber 152 and other downstream elements to be isolated from and at different pressures with respect to aerosol generator 100. Elastomer gland 130 seals by virtue of the spring 154 force applied to it by washer 135. Spring 157 is held in place within the delivery tube 153 and the delivery tube assembly 155 is held together by cap 137. All elements of the aerosol individualizer 100 are rigidly and precisely machined and aligned, but many support and assembly elements are omitted for clarity of illustration.

B. Rotary. Metering Pocket

Figure 5:
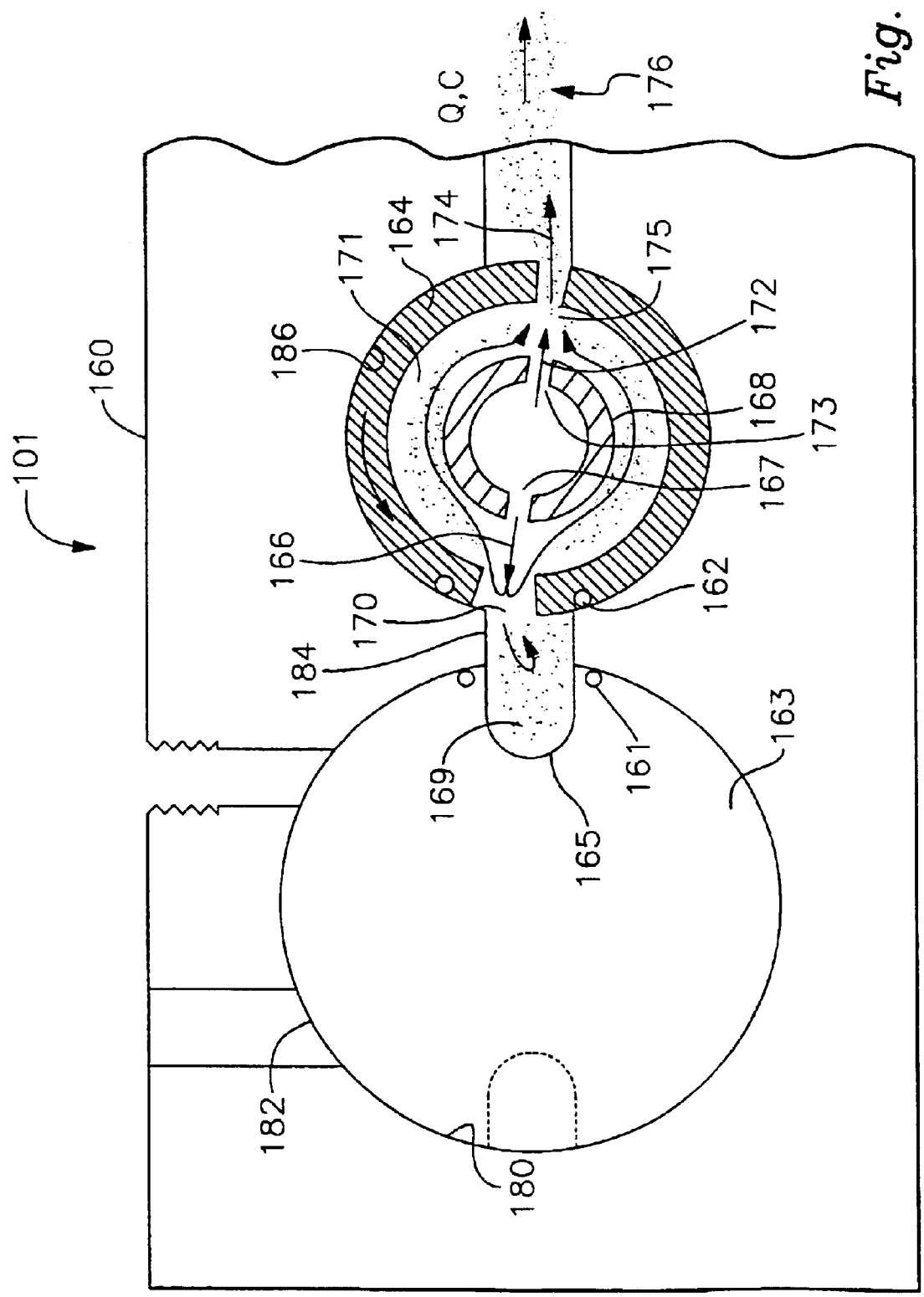
FIG. 5 shows elements of another aerosol generator embodying the invention.

FIG. 5 shows a second embodiment 101 of an aerosol generator. Aerosol generator 101 comprises a body 160 in which are precisely installed, with tight seals 161 and 162, a powder pocket cylinder 163 within a powder pocket cylinder cavity 180 within the body 160, and a metering cylinder 164 within a metering cylinder cavity 186 within the body 160. One of a large plurality (tens to thousands) of powder "pockets" 165 is shown in pocket cylinder 163. The plurality of pockets 165 is machined into pocket cylinder 163 by any suitable method, such as precision drilling.

In close and precise proximity to powder pocket 165, and communicating via a passageway 184 within the body 160, are the metering cylinder 164 and fluidizing and first individualizing or deagglomerating jet 166 emanating from orifice 167 in high pressure delivery tube 168. First stage aerosolization, meaning fluidization of powder 169 in pocket 165, in combination with turbulent, counterflow deagglomeration by individualizing jet 166, is achieved in concert with controlled or metered release of powder 169 through variably open hole 170 and action of variably directed and energized jet 166.

This metered aerosolization may also be referred to as "microscooping," as in the previous embodiment. In general, "aerosolization" is referred to herein as the combined fluidization, individualization, and transport of the aerosols, be they derived from bulk powders, as in these first three embodiments, or atomized liquids, as disclosed hereinbelow with reference to FIG. 10.

Mass delivery rate dM/dt of powder 169 from powder pocket 165 is metered or controlled by gradually increasing opening 170 by rotating metering cylinder 164 and controlling the direction and intensity of jet 166. Intensity is controlled by controlling the pressure within delivery tube 168. Aerosolized powder plus gas flow or move within the pressurized space 171.

A second jet 172, emanating from orifice 173, further individualizes powder 169 and supplies additional gas flow and energy. The orifices 167 and 173 are drilled into high pressure delivery tube 16B. Individualizing jet 174, emanating from orifice 175, comprises a third stage of deagglomeration. The flow in jet 174 is the combined flows from of jets 166 and 172. Note that jet 174 moves in the same direction as aerosolized particles 176, in contra distinction with the counterflow movement with respect to jet 166.

The output 176 from aerosol generator 101, in the form of an expansive bolus 176, is delivery of aerosolized powder having high average concentration C in known volumetric flow rate Q of the aerosolizing/transport gas. This aerosol generator system 101 is appropriate for multiple deliveries, whereas the microscoop aerosol generator 100 apparatus disclosed above (FIGS. 1, 2) is more appropriate for single or a few deliveries. Representative dimensions and operational parameters for aerosol generator 101 and its output delivery 176 are:

| | |
|---|---|
| Volume of Powder Pocket 165 | ~1 mm³ |
| Weight of powder in Pocket 169 | 250 µg |
| Diameter of Picket Cylinder 163 | 25 mm |
| Diameter of Metering Cylinder 164 | 10 mm |
| Diameter of Gas Delivery Tube 168 | 5 mm |
| Diameter of Orifices 167 and 173 | 0.25 mm |
| Diameter of Orifice 175 | 0.35 mm |
| Pressure of Gas in Delivery Tube 168 | 10 bar |
| Pressure of Gas in Fluidizing Chamber 171 | 5 bar |
| Duration of Pressure Pulse in Tube 168 | 100 ms |
| Rate of Pressure Pulses | 1/sec |
| Volumetric Flow Rate Q during Pressure Pulse (=167 × 10⁻⁶ m³/sec = 10 liters/min) | 167 cm³/sec |
| Mass Concentration C during Pressure Pulse (250 × 10⁻⁶ g/167 × 10⁻⁶ m³ sec × 0.1 sec) | 15 g/m³ |

Pulsed pressure operation as short as 10 ms is possible, as is continuous operation.

Materials of construction are as follows:

| | |
|---|---|
| Body 160 | Nylon, Delrin or UHMW |
| Pocket Cylinder 163 | Al |
| Metering Cylinder 164 | SS |
| Pressure Tube 168 | SS |

Figure 6A:
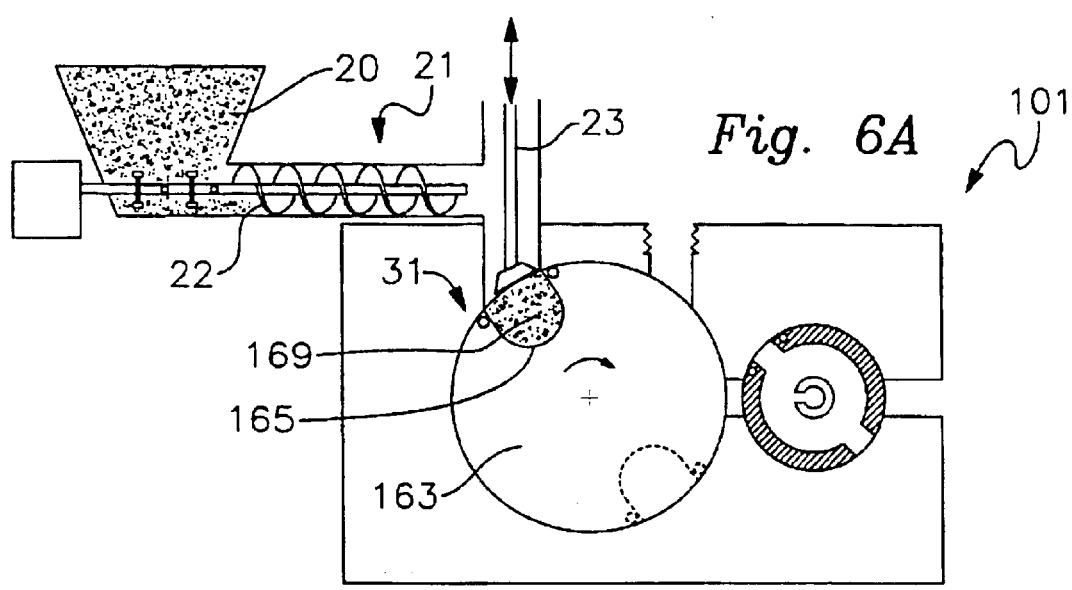
FIGS. 6A, 6B and 6C depict successive steps in the operation of the FIG. 5 aerosol generator.

FIG. 6A depicts loading step 21, symbolized as 11 in FIG. 1, for introducing bulk powder 20 into each of the plurality of pockets 165 in pocket cylinder 163. Powder loaded into pockets 165 is designated 169. Loading apparatus 21 includes a metering auger 22 and tramper or packer 23. The bulk powder 20 thus transferred to pocket 165 when powder chamber cylinder is in loading position 31.

Figure 6B:
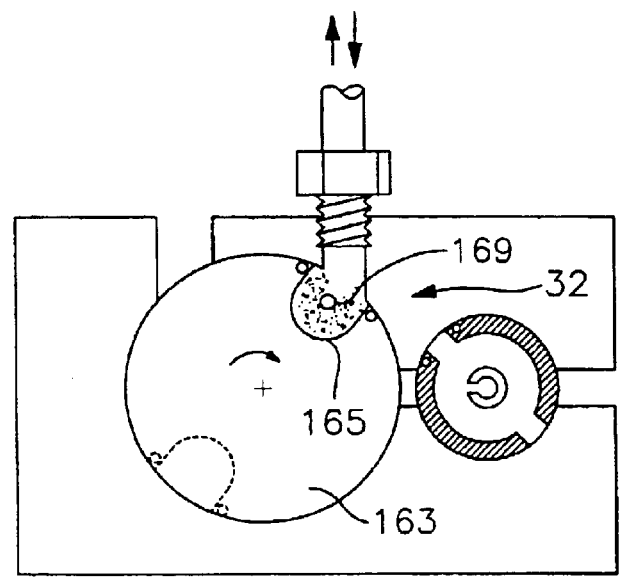

FIG. 6B illustrates a preconditioning position 32 of typical pocket 165 in pocket cylinder 163. Preconditioning is done by, for example, slowly drawing a vacuum and then slowly repressurizing pocket 165 with another gas. Slow pressure changes are necessary to avoid fluidizing the powder prematurely.

Figure 6C:
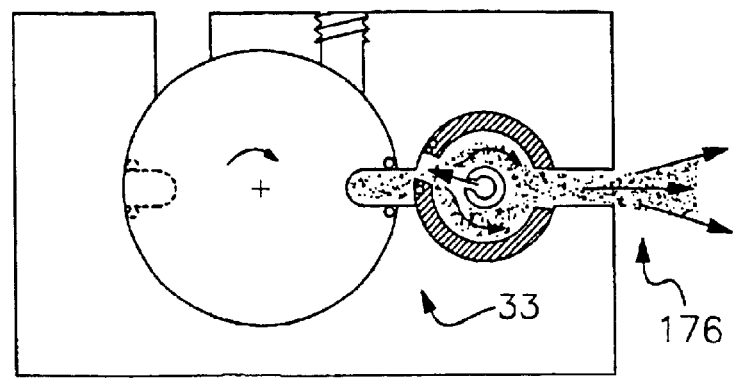

FIG. 6C, where the pocket 165 is in active position 33, is functionally the same as FIG. 5 except second and third stage individualizing jets 172,174 are omitted. This is satisfactory for powders which are relatively large and easy to deagglomerate or individualize and enables a simpler and less expensive apparatus.

Figure 7:
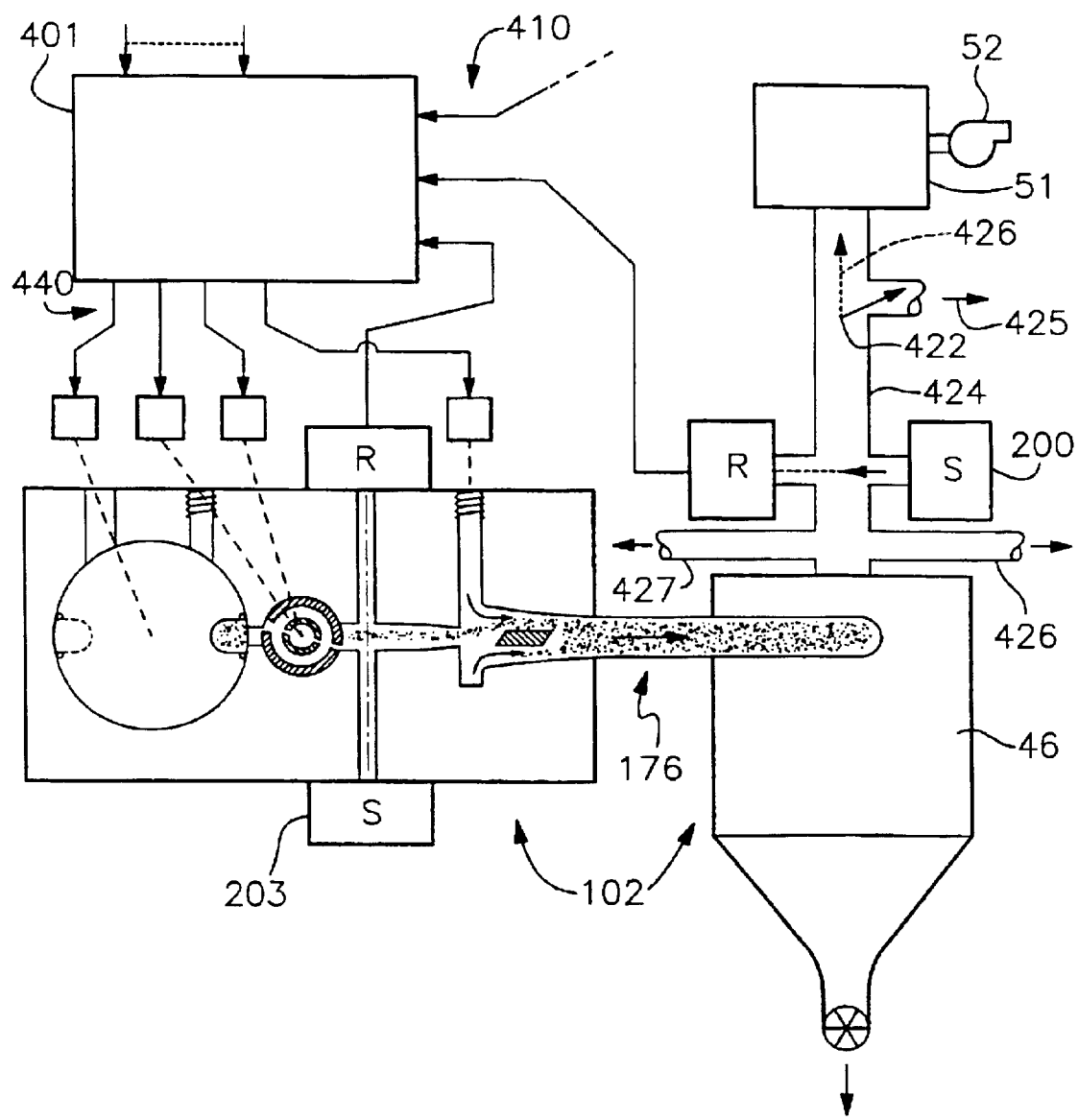
FIG. 7 shows another aerosol generator embodiment.

FIG. 7 shows a more complete aerosol generator system 102, including a cyclone 46 and, schematically, a measurement and control system 401, similar in function to the CCM 400 in FIG. 1. Aerosol Generator 102 in FIG. 7 is like the aerosol generator 101 of FIG. 6C with the addition of high pressure impaction stage 42, for the most aggressive deagglomeration. Also shown are sheath gas 44 to minimize wall deposition. Cyclone 46 acts as a mixing, stilling, and classification chamber, similarly to mixing chamber 152 in FIG. 2. Large particles are removed from the bottom of cyclone 46.

Further shown in FIG. 7 are electro-optical mass concentration sensor 200, which are physically identical and function identically to electro-optical sensor 200 in FIG. 1, and electro-optical mass concentration sensor 203, which is physically similar and functions as a preliminary monitoring element, thus enabling faster response to output fluctuations in aerosol generator 100. Such sensors are manufactured by ppm, Inc., Knoxyille, TN. Also shown in FIG. 7 is a microcontroller-based computer 400, which may be identical to CCM 400 of FIG. 1. Various inputs 410 and outputs 440 are used to monitor and control the deliveries of aerosolized mass and flows, as described above.

With particular attention to one 424 of the plurality of deliveries 424, 426, 427 diverter valve 422 causes the aerosols and gas flow in delivery 424 to move in direction 425 toward a deposition zone (not shown in FIG. 7) or in direction 426, toward the HEPA filter 51 and suction device 52. These latter elements 51, 52 are identical with those in FIG. 1. Two other deliveries 426, 427 illustrate the plurality of deliveries for which aerosol generator 100 in FIG. 7 is capable of serving. Each such delivery has similar elements as delivery 424, including downstream sensors 201, as in FIG. 1.

Each output 424, 426, 427 of aerosol generator 102 is an aerosolized powder having controllable mass concentration C (g/m³) in transport gas having independently controllable and known volumetric flow rate Q (m³/sec). Thus aerosol generator 102, in each of its plurality of deliveries such as delivery 424, obeys basic control Equation (4), above.

C. MegaDose Disc

Figure 8:
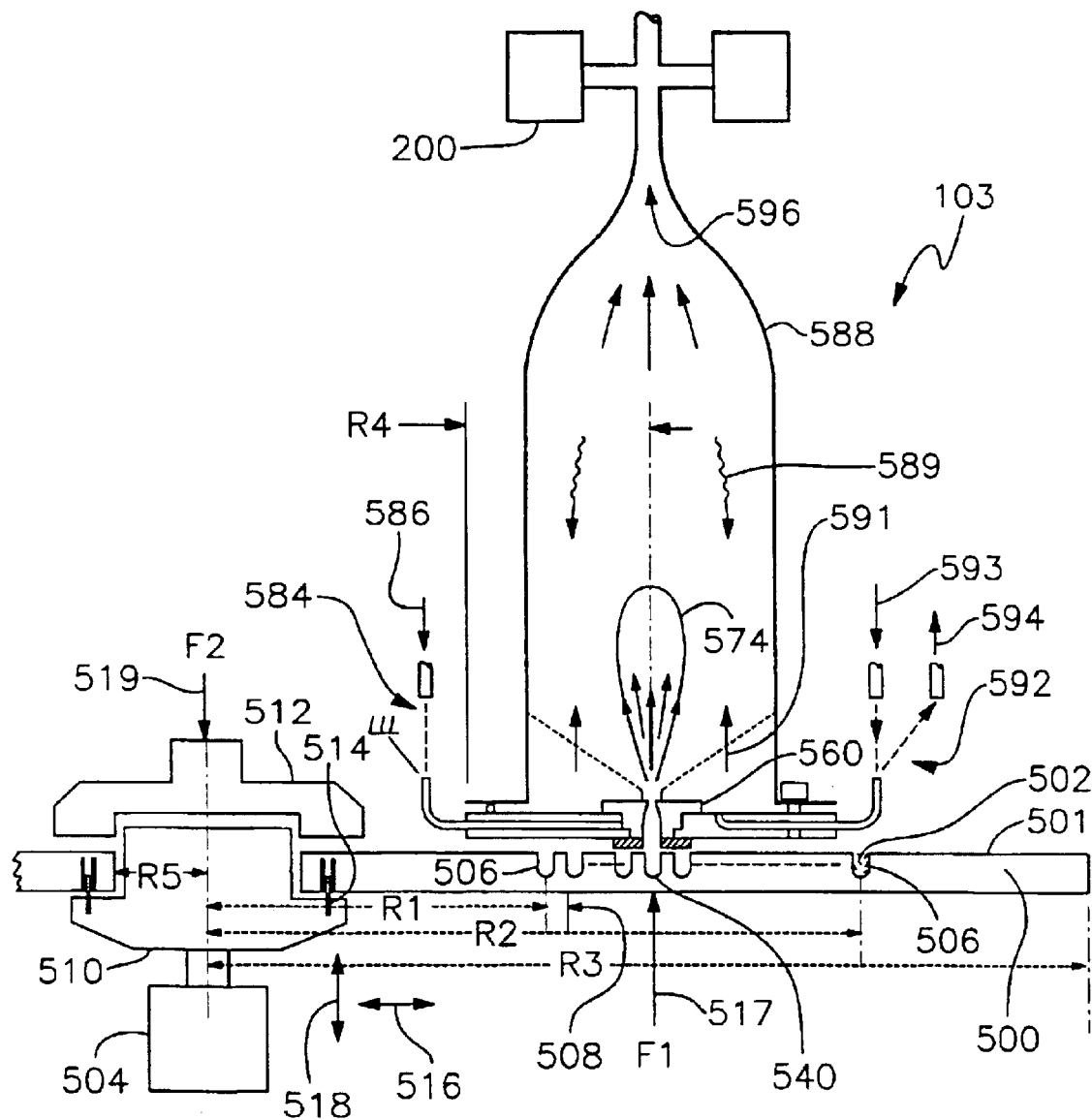
FIG. 8 shows yet another aerosol generator embodying the invention.

FIG. 8 is an elevational, partially cut-away view of a third embodiment of an aerosol generator 103, also directed to aerosolization of bulk powders, as were the previous two. In a preparation step, bulk powder is loaded into a large plurality (~10,000) of metering pockets 506 formed in surface 501 of disc 500. Each metering pocket 506 has diameter of about 0.5 mm, a depth of about 10 mm, a volume of about 2 mm$^3$, and each holds about 1 mg=1000 μg of bulk powder 502. Each pocket 506 can supply 100×10 Ag doses, hence the name "MegaDose Disc." It may be appreciated that these discs can supply either more smaller doses or fewer larger doses. It may also be appreciated that such discs, with suitable covers and protection, are ideal for transport and storage of expensive and sensitive powders.

A stepper motor 504 having 0.9 degree/step or 400 steps/revolution is used to drive disc 500, with 1 mm minimum spacing between pocket centerlines. The minimum radius R1 is then 64 mm. Each pocket circle has 400 equally spaced pockets but, whereas the angular spacing between pockets is constant at 0.9 degrees, the physical spacing increases as the radius of the pocket circles increases. If, as a representative example, 10,000 pockets are desired, then 25 pocket circles are required. A constant spacing between the successive pocket circles of 1 mm 508 leads to the outer pocket circle having R2=64+24=88 mm. The outer radius of the disc R3=R2+R4=88+40=128 mm. R4=40 mm is the outer radius of the mixing/stilling/classifying chamber 588 seen in FIG. 8.

The inner radius R5 of the disc mounting hole is about 24 mm. This 48 mm diameter hole fits tightly over hub 510 and is held in position by top cap 512. Rotational alignment and drive pins 514 assure that the active pocket 540 is always directly under fluidizing body jet 560, with the very tight tolerances required, in combination with transverse stepping motion 516, where the steps are precisely 1 mm each. Unshown apparatus applies an upward, sealing force F1 517 to disc 500, except during disc 500 rotation or translation. Stepper motor 504 and hub 510 permit vertical motion 518 for installing and removing discs 500. Force F2 519 is applied to top cap 512 to assure proper drive torque without slippage.

Figure 9:
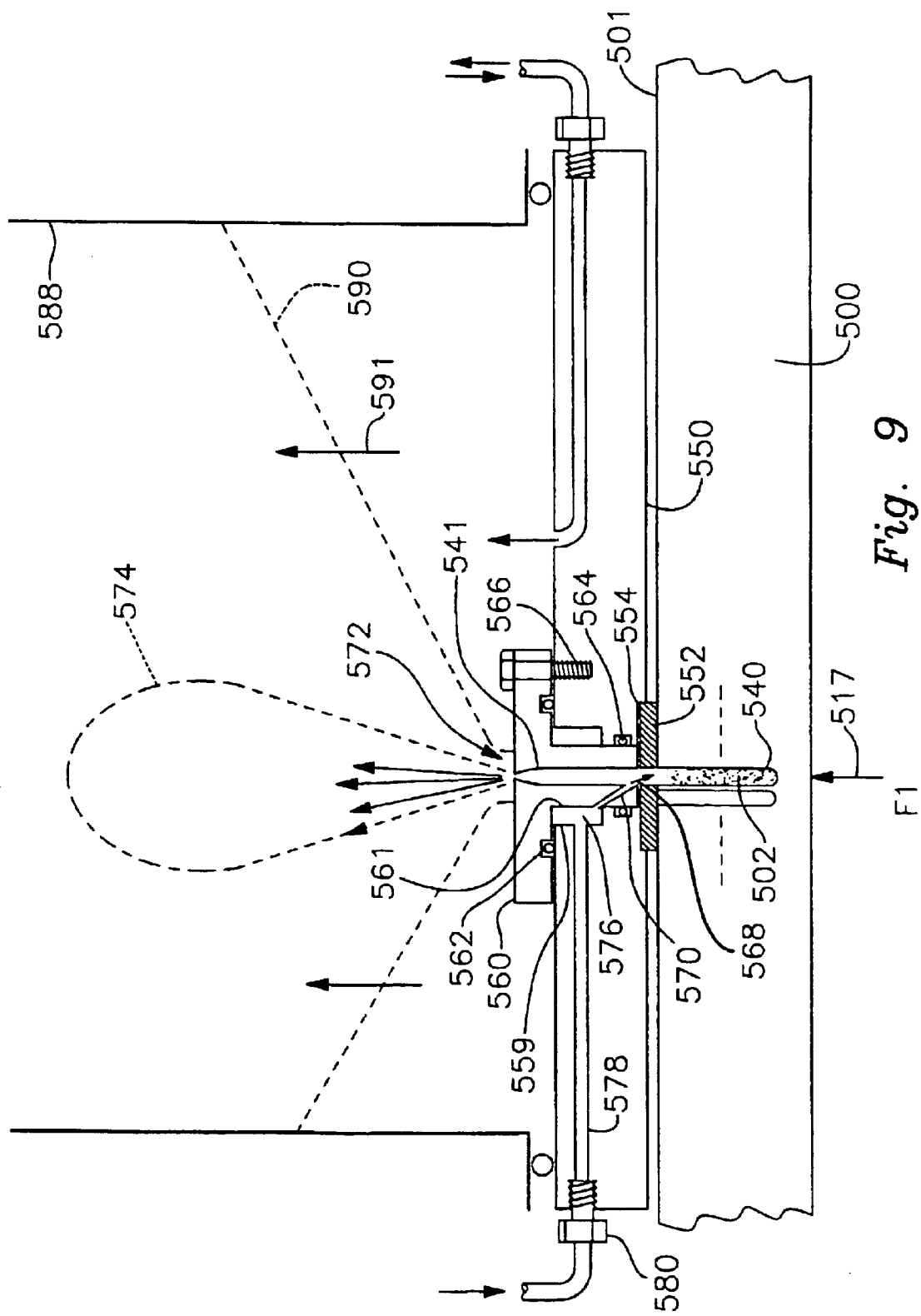
FIG. 9 is an enlarged view of the aerosol generator of FIG. 8 in the vicinity of the active pocket.

FIG. 9 is an enlarged view around active pocket 540, one other of the plurality of pockets 506. Disc 500 is pressed upward against baseplate 550 by force F1 517. Sealing around active pocket 540 is realized by elastomer washer 552 seated in counterbore 554. Pocket jet body 560 is sealed into baseplate 550 by O-rings 562, 564 and is held in place by multiple cap screws 566, only one of which is shown. Fluidizing/deagglomerating jet 568 emanates from orifice 570 and acts on powder 502 in active pocket 540, driving it outwards, in a turbulent, counterflow sense. Energization of this jet 568 is explained below. Exit orifice 572 in the top of pocket jet body 560 restricts the egression of powder and gas, thus further deagglomerating the powder by the "turbulent milling" action driven by jet 568 within pocket 540 and by its extension 541 into body 560, and causes elevated pressures within the pocket 540. These higher pressures cause the gas to expand upon leaving orifice 572 and thereby effect more aggressive deagglomeration. Orifice 572 diameter is preferably about 0.35 mm when the pocket 540 diameter is about 0.5 mm.

The "expansive bolus" 574 of gas and powder and the other components above the pocket jet body 560 are discussed again hereinbelow, following an explanation of how pocket jet 568 is energized. The expansive boli 150, 176, 574 of FIGS. 2, 7 and 8, respectively, are a common element of the disclosed aerosol generators 100, 102 and 103.

Orifice 570 is in pocket jet body 560 and is the orifice from which pocket jet 568 emanates. Orifice 570 may be drilled in the body 560, or a capillary, preferably stainless steel, may be glued into a pilot hole. Multiple orifices 570 may be used. Orifice or capillary internal diameters are in the range of 0.25 mm. A feeding plenum 576 is formed between the lower section 561 of pocket jet body 560 and a counterbore 559 in the baseplate 550. Pressurized gas is delivered to the feed plenum 576 by coupling hole 578 which is connected to fitting 580. Referring also to FIG. 8, solenoid valve 584, upon being electrically energized, connects the pocket jet 568 feed system 580, 578 to the high pressure gas supply 586, about 10 bar. Pulse durations of about 10 ms usually sweep out the powder 502 in pocket 540 in a single pulse, typically, but the number of pulses and their duration depends on the powder being aerosolized. Continuous operation of jet 568 may also be employed.

Still referring to FIG. 8, the expansive bolus 574 resulting from such short pulses represents a small fraction, typically 1–10%, of the volume in mixing/stilling/classification chamber 588. The mixing chamber 588 thus stills and mixes the bolus just delivered with boli delivered earlier. There is a classification feature, as particles whose Stokes settling velocity is higher than the upward flow velocity "elutriate out" or simply fall down, as indicated by wavey arrows 589. In most applications it is desirable to assure that particles larger than some preselected cut-off are not in the effluent from the mixing/stilling/classification chamber 588. For 1 liter/min upward flow in chamber internal diameter of 75 mm, the upper cut-off is an aerodynamic equivalent particle diameter of about 11 μm.

The upward flow component is provided by steady flow 591 through perforated flow distribution plate 590, which total flow 593 is supplied by solenoid valve 592.

In some cases, when impulsive flow from orifice 572 is used and the flow and pressure fluctuations cannot be controlled by downstream apparatus or is otherwise unacceptable, solenoid valve 592 is also connected to a negative pressure or suction 594 and is operated in synchronism with energization of the pocket jet 568, in a "push-pull" manner that minimizes or cancels pressure and flow fluctuations.

With reference to FIG. 8, the smooth transition and inlet 596 from the mixing/stilling/classification chamber 588 into the first sensor bore 200 has practical importance. Experience has shown that this transition is important for the validity of the scalar calculation of mass delivery rate dM/dt discussed above.

D. Atomized Liquid

Figure 10:
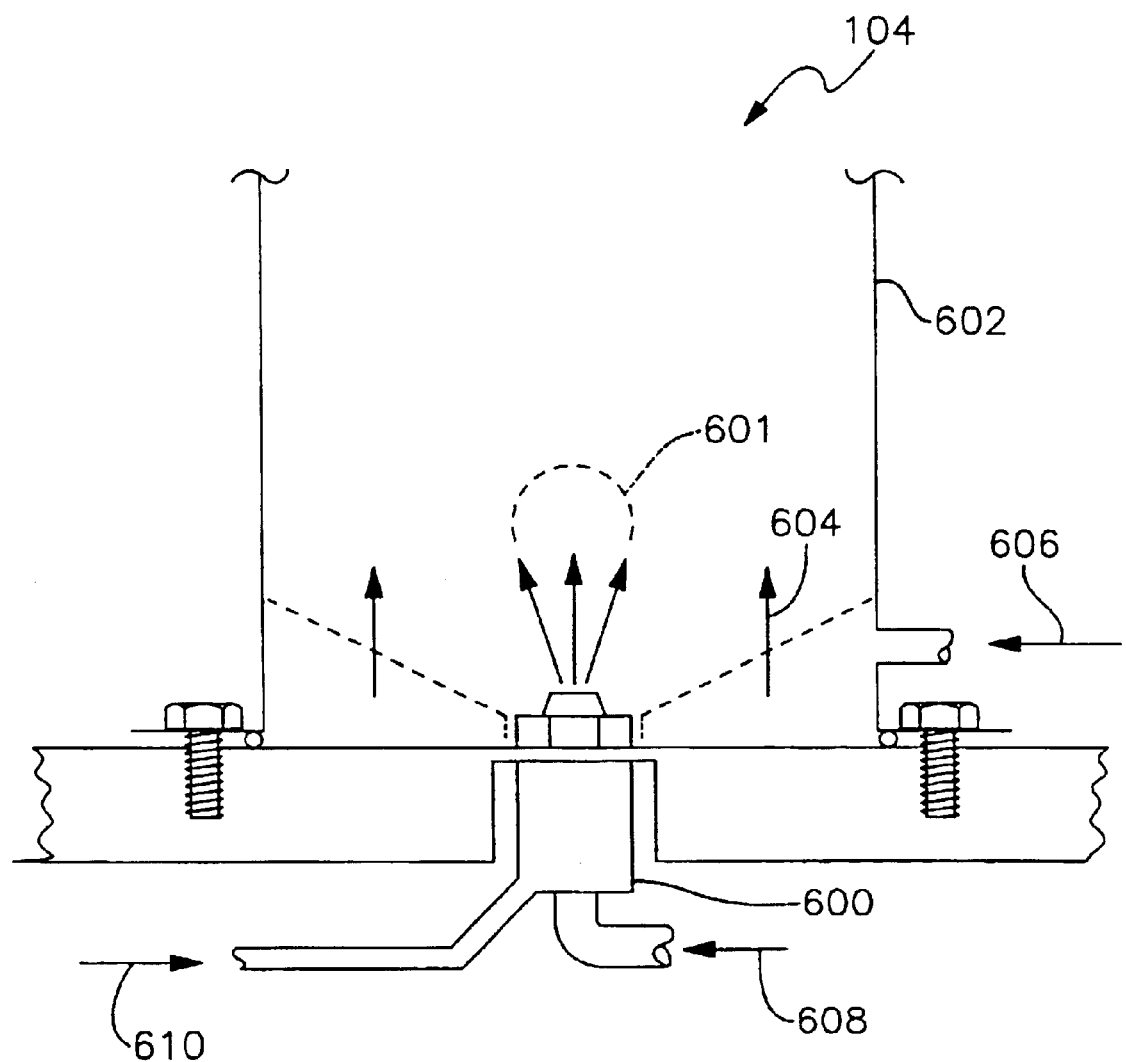
FIG. 10 depicts an embodiment involving the injection of pulsed, expansive boli of aerosols and gas.

FIG. 10 discloses another aerosol generator embodiment 104 which likewise involves injecting expansive boli of aerosols and gas 601 into a mixing/stilling/classification chamber 602. Two-fluid atomizer nozzle 600 injects, impulsively or continuously, its boli into mixing chamber 602, which functions essentially identically as mixing chamber 588 described above with reference to FIGS. 8 and 9, including provision of steady, upward gas flows 604 derived from supply 606. Operation at the "micropocket" level is also essentially identical, wherein aerosolizing (or "atomizing" for liquids) is effected in pocket volumes of under 1 mm$^3$, with high velocity jets.

Atomizing gas 608 and transporting gas 604 may be different in composition or initial temperature. The active ingredient is delivered in liquid solution 610. Upon impulsive or continuous excitation of the atomizer 600, the droplets in the boli rapidly evaporate the solvent into the gaseous phase, leaving the solute residue as the active aerosol whose mass deliveries are precisely and accurately controlled exactly as disclosed above.

The embodiment of FIG. 10 is important for a number of reasons, a significant one of which is that the aerosols are actually manufactured within aerosol generator 104, thus avoiding the difficulties and expenses of separately manufacturing and handling bulk powders, only to reaerosolize them again. This is particularly advantageous when the feedstock 610 for the aerosols is a dilute solution, with a volatile solvent.

Still referring to FIG. 10, the bottom inlet of mixing/stilling/classifying chambers 602 may be connected directly to any processes wherein dry or wet aerosols are being manufactured. By causing the concentrations C and flow rates Q, which are required in the disclosed embodiments of the invention for controlled deliveries, to be compatible with the manufacturing process, then the bulk formation and handling of the powders can also be bypassed.

3. Deposition or Collection

A. Porous Media

Figure 4A:
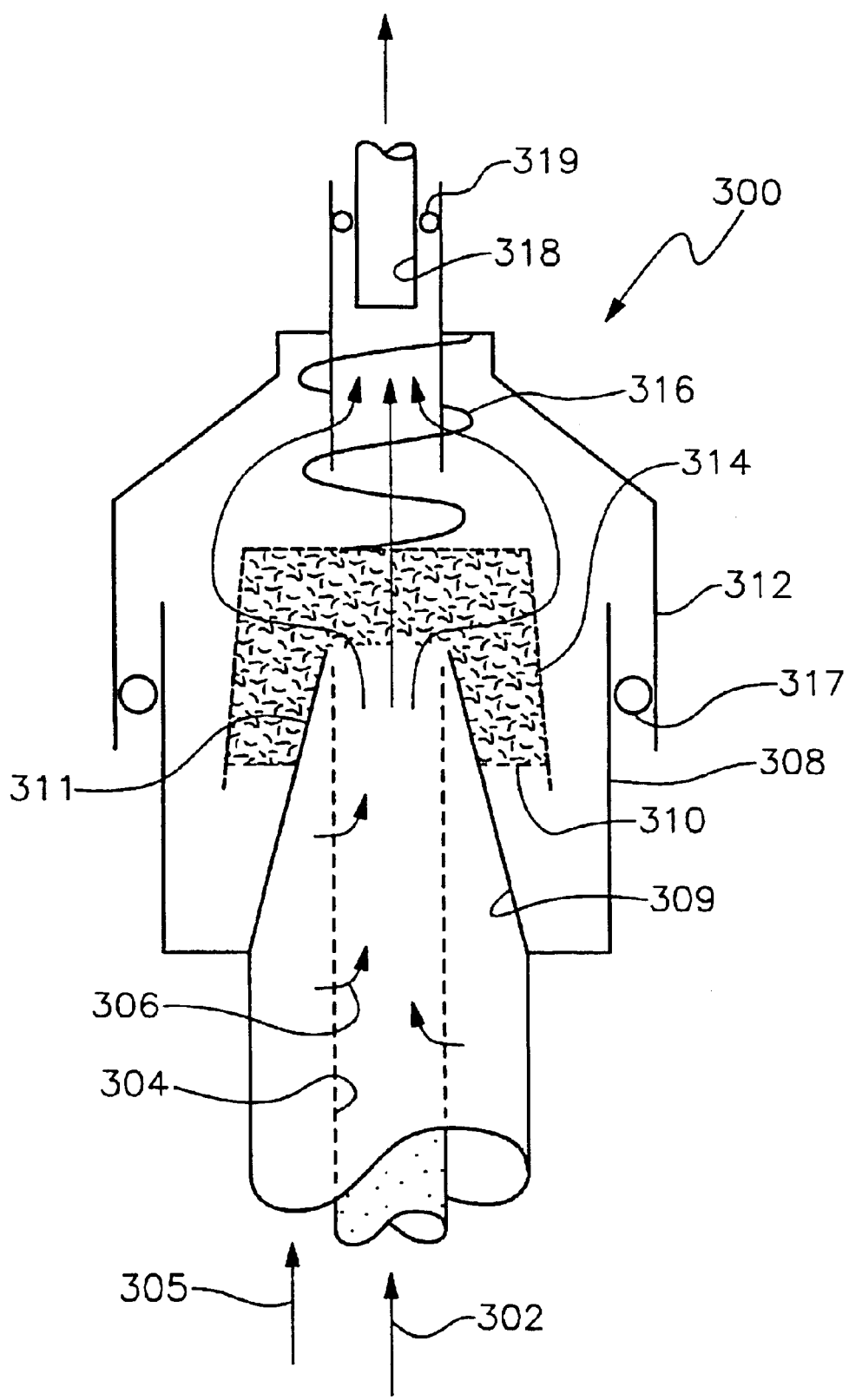
FIG. 4A is an enlarged view of a deposition zone including a porous media collection element.

FIG. 4A is an enlarged view of the deposition zone 300 and better shows inert, porous media collector 310, as seen first in FIG. 1, with the system closed and in the aerosolized mass delivery-collection mode. This collection element 310 resembles a small inverted, porous cup with tapered interior surface 311 which matches and thus seals to the taper of tube 309. Perforated metal cup 314 fits around the outside of inert media collector 310 to support it and also has a tapered surface to provide a sealing force against the taper 309, and to enable transport gas to be drawn (or pushed and drawn, with positive and negative pressures, respectively), through the upstream and downstream surfaces of inert media collector 310. The sealing force is provided by spring 316. Outer shell 312 seals against inner shell 308 and pipe 318, both with elastomer O-rings.

The mechanical material properties of inert media collector 310 that are important for collection are: dry strength, porosity or permeability, capture efficiency for the active component collected, and costs. Preferably, when the active component is a dry powder having mass mean diameter of 10 micrometers, the incipient media collector is a powder having particle size about 200 micrometers, thickness of about 1 mm, and weight of about 100 mg. Care must be taken in selection and application of binder agents in the manufacture of porous media 310. Such agents must be satisfactory for human use and also must not diminish the permeability of collector 310 excessively. Active component loading should not exceed 10 mg and the aerosol generation section will need to operated at lower transport flows Q. Capture efficiencies for such collectors can approach 100% for the large particle size indicated above. However, if the delivered aerosol mass mean diameter is below about 1 $\mu$m, the capture efficiency drops and it is necessary to correct for the mass delivered but not captured and retained, according to the methods described hereinabove.

The requisite properties for subsequent use include suitable for human consumption, shelf life, interactions with the active component, inertness, solubility, and the like.

B. Impactive Deposition

Figure 4B:
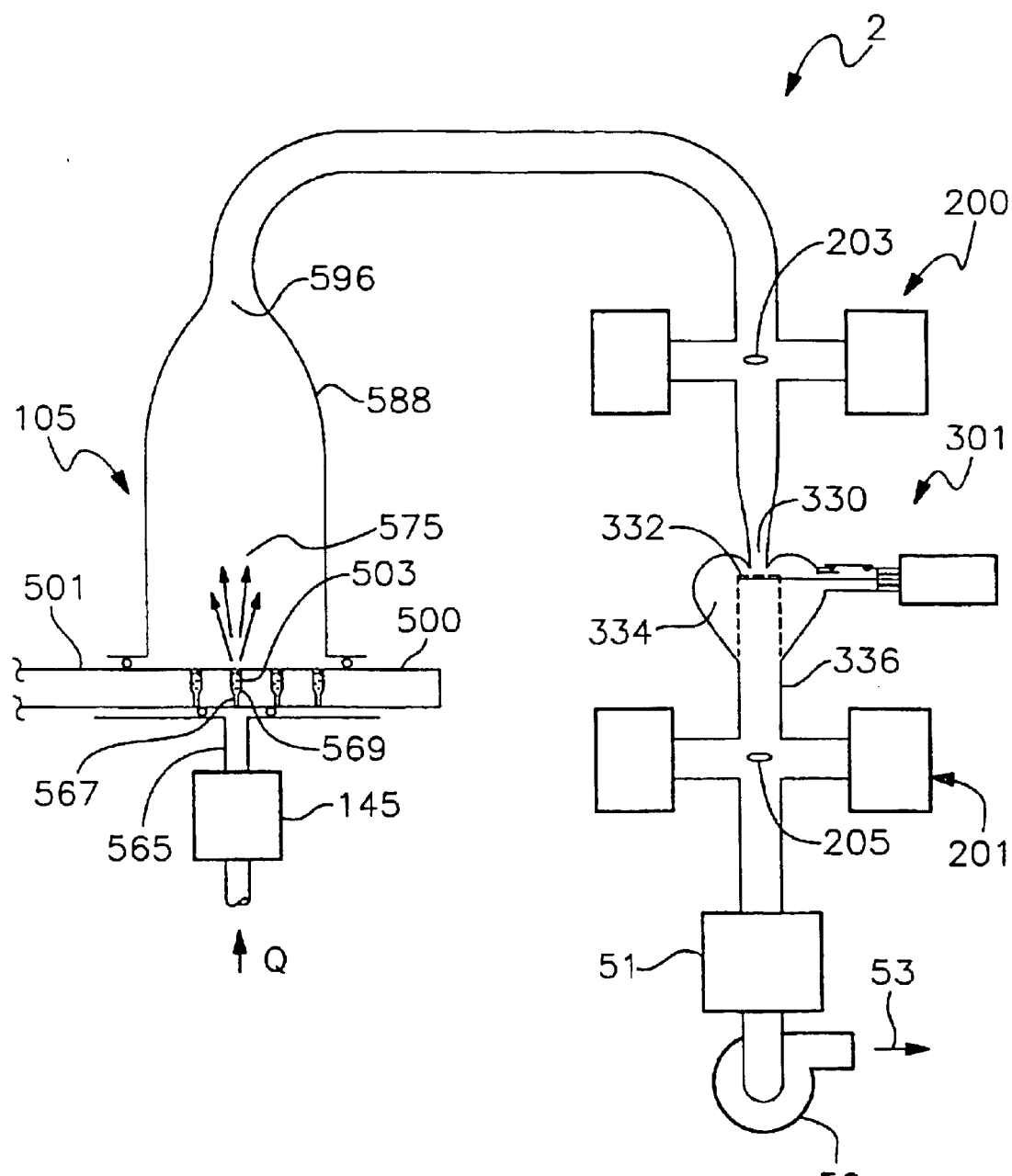
FIG. 4B is a schematic depiction of a system embodying the invention and including an impactive deposition zone.

FIG. 4B illustrates a system 2 for controlled aerosolized mass delivery comprising, similar to FIG. 1 system 1, and comprising aerosol generator 105, upstream and downstream mass concentration sensors 200, 201 and deposition zone 301, described in more detail hereinbelow. Not shown in FIG. 4B is control and communications module 400 of FIG. 1 and connections thereto. In FIG. 4B, aerosol generator 105 employs a MegaDose Disc 500 as described hereinabove with reference to FIGS. 8, 9, but with the aerosolizing gas flow Q entering the bottom of pocket 569, via orifice 567.

Differences of the embodiment of FIG. 4B compared to the embodiments of FIGS. 1, 2 and 8 include the absence of perforated walls 107, 154 and inward, additional flows associated therewith. Thus, the continuous or impulsive aerosolizing gas flow Q, measured by volumetric flow rate sensor 145 and, importantly, reported to CCM 400, and adjusted to the pressure and temperature conditions within sensor 200, is the correct known volumetric flow rate for calculating upstream mass delivery rate dM/dt=QC. For emphasis, it is necessary that the known Q be in terms of volumetric flow rate at the point at which C is measured, as in upstream sensor 200. It is not necessary to actually measure Q at that point. These concepts apply to the determination of all other mass delivery rates herein.

As an illustrative example, the pressure and temperature in volumetric flow rate sensor 145 may be 20 bar and 21° C. This aerosolizing gas is delivered to orifice 567 via coupling conduit 565. Aerosolizing action upon powder 503 in pocket 569 is effected by high velocity jet emanating from orifice 567, thus driving expansive bolus 575 into mixing chamber 588. After pressure and thermal equilibration, aerosolized powder 503 (from one or more pockets 567) and transporting gas arrive at the measurement zone 203 of upstream mass concentration sensor 200, where the pressure may be 1 bar and the temperature 21° C. Accordingly, the known volumetric flow rate Q inside sensor 200 is expressed in terms of local pressure and temperature but it can be measured anywhere in the system, such as shown by sensor 145 in FIG. 4B. (In this example, the actual volumetric flow measure within and by volumetric flow rate sensor 145 is one-tenth that inside mass concentration sensor 200, according to gas law corrections.)

Figure 4C:
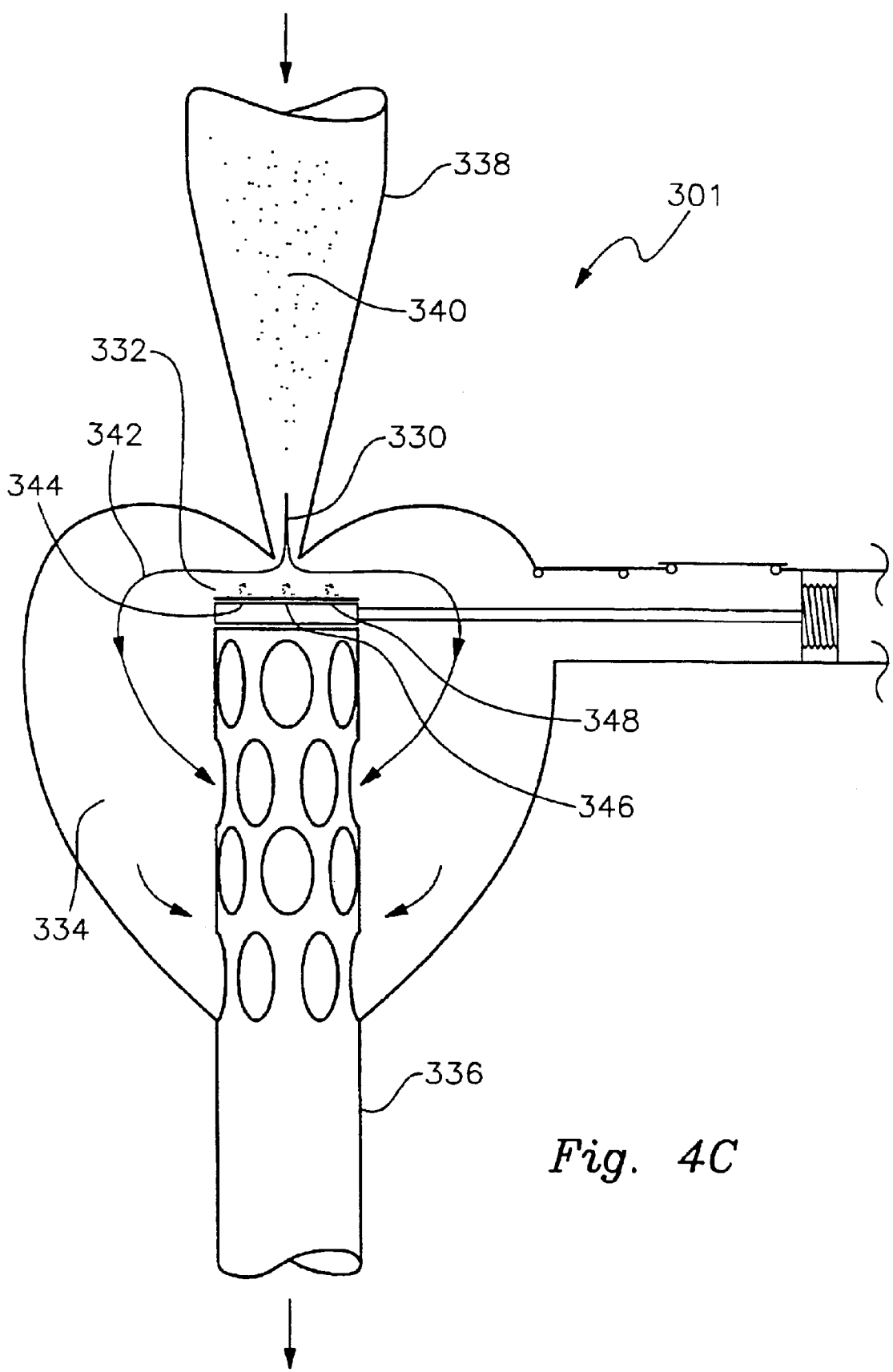
FIG. 4C is an enlarged view of an impactive deposition zone with multiple deposition areas.

FIGS. 4B and 4C illustrate, in deposition zone 301, deposition or collection devices using principles of aerosol impaction primarily comprising impactor jet 330, impactor plate 332, downstream plenum or suction plenum 334, and output conduit 336. Filter 51 and pump 52 perform the same functions as in FIG. 1 but pump 52 must operate at strong suction (<0.5 bar) if the pressure in sensor 200 is 1 bar, essentially the same as the pressure entering impactor nozzle 338. When the impactor upstream/downstream pressure ratio exceeds 2:1, the velocity of impactor jet 330 approaches sonic velocity or Mach 1. If the taper of nozzle 338 is gradual, less than about 3°, aerosols 340 accelerate and approach the high velocity of impactor jet 330. Aerosols 340 above a "cut-off" size cannot follow the flows 342 across the impactor plate 332 and are deposited on or collected by impactor plate 332 in deposition area 346. Particles 340 larger than 5 $\mu$m are readily collected with greater than 90% efficiencies on impactor plate 332 when impactor jet 330 velocity is greater than Mach 0.3. The delivery rate of particles not collected on impactor plate 332 and transported into output conduit 336 and to downstream sensor 201 are measured to determine the net deposition, according to Equation (5) and the methods thereto related and described hereinabove. The volumetric flow rate used in combination with downstream mass concentration sensor 201 must be at the pressure and temperature conditions in measurement zone 205 within sensor 201. This known flow rate Q can be measured at those conditions or determined elsewhere and corrected to those conditions, as described above.

Figure 4D:
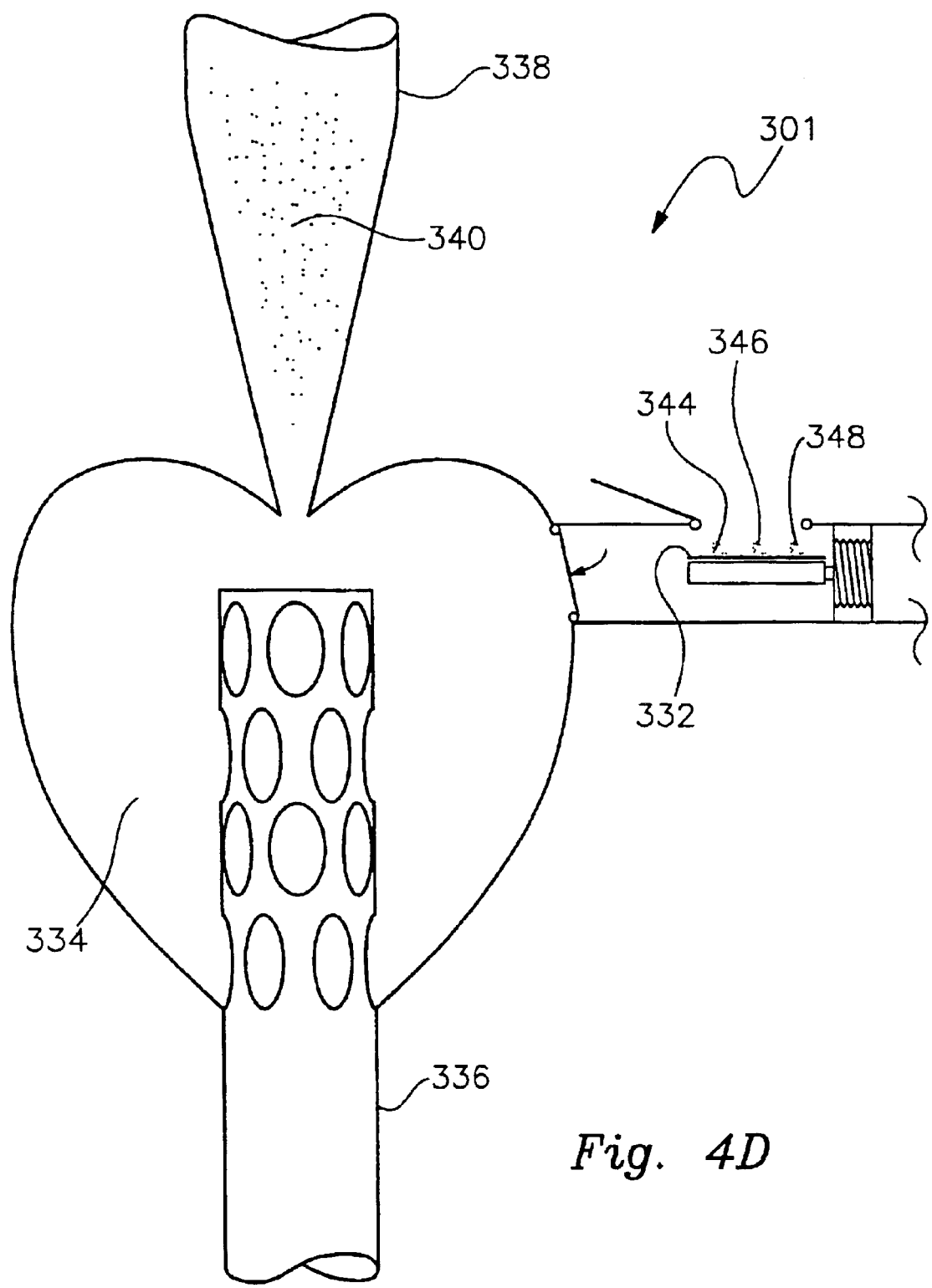
FIG. 4D is an enlarged view similar to FIG. 4C, illustrating the removal of the deposition areas following deposition.

FIG. 4C shows multiple deposition areas 344, 346, 348 on impactor plate 332. Impactor plate 332 may be of any material suitable for human contact or consumption but relatively soft or waxed or oiled plastic is preferred. The aerosolized mass dosages in deposition areas 344, 346, 348 seen in FIG. 4D are the final product of the controlled delivery and deposition apparatus. These deposition areas are accessible for removal upon transfer out of deposition zone 300 by straightforward translation and gas system isolation devices shown in FIGS. 4C (closed) and 4D (open).

C. Electrostatic Collection

Figure 4E:
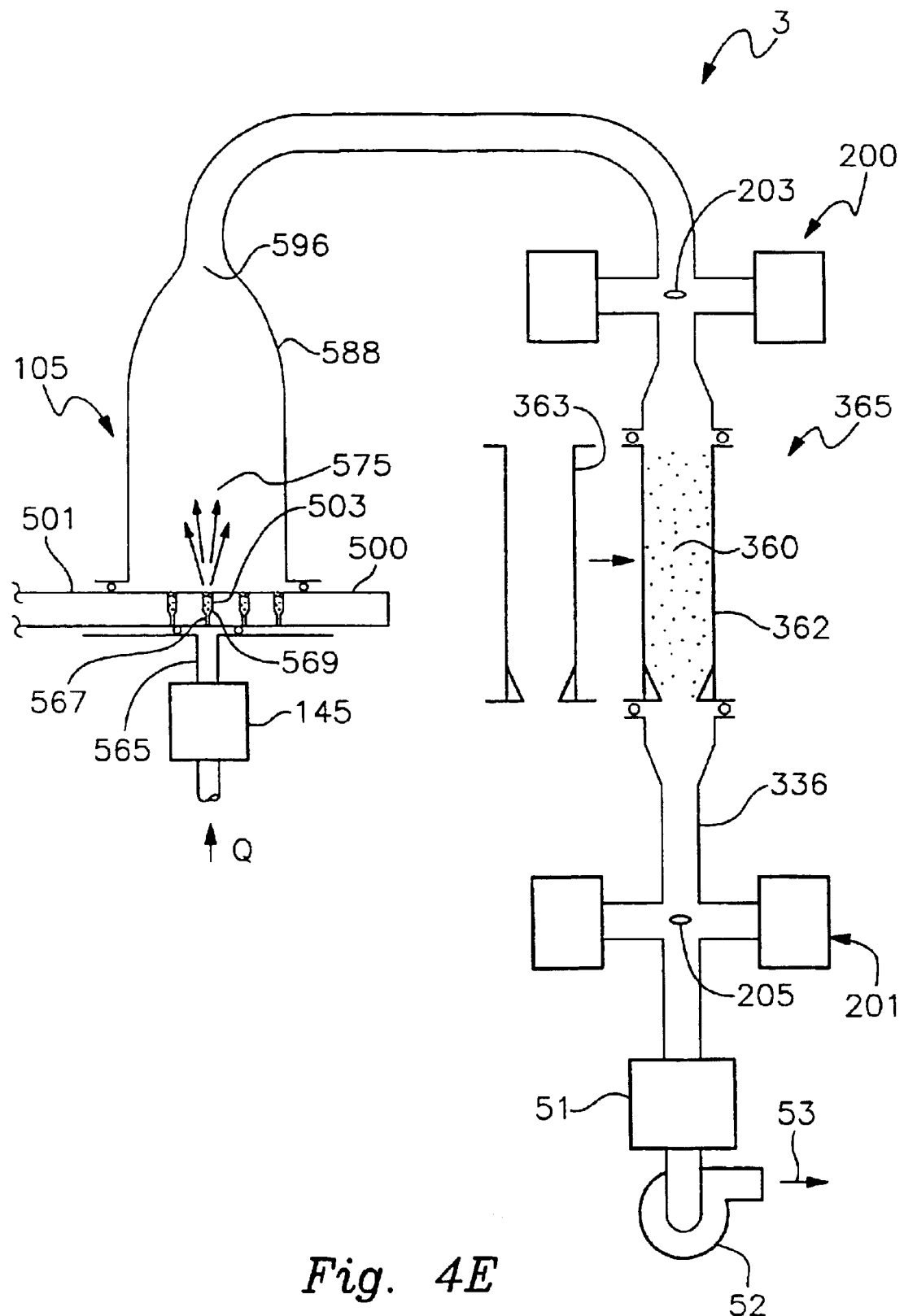
FIG. 4E is a schematic depiction of a system embodying the invention and including a mass delivery section for loading an aerosolized mass into a removable drift tube as an element of a deposition zone.
Figure 4F:
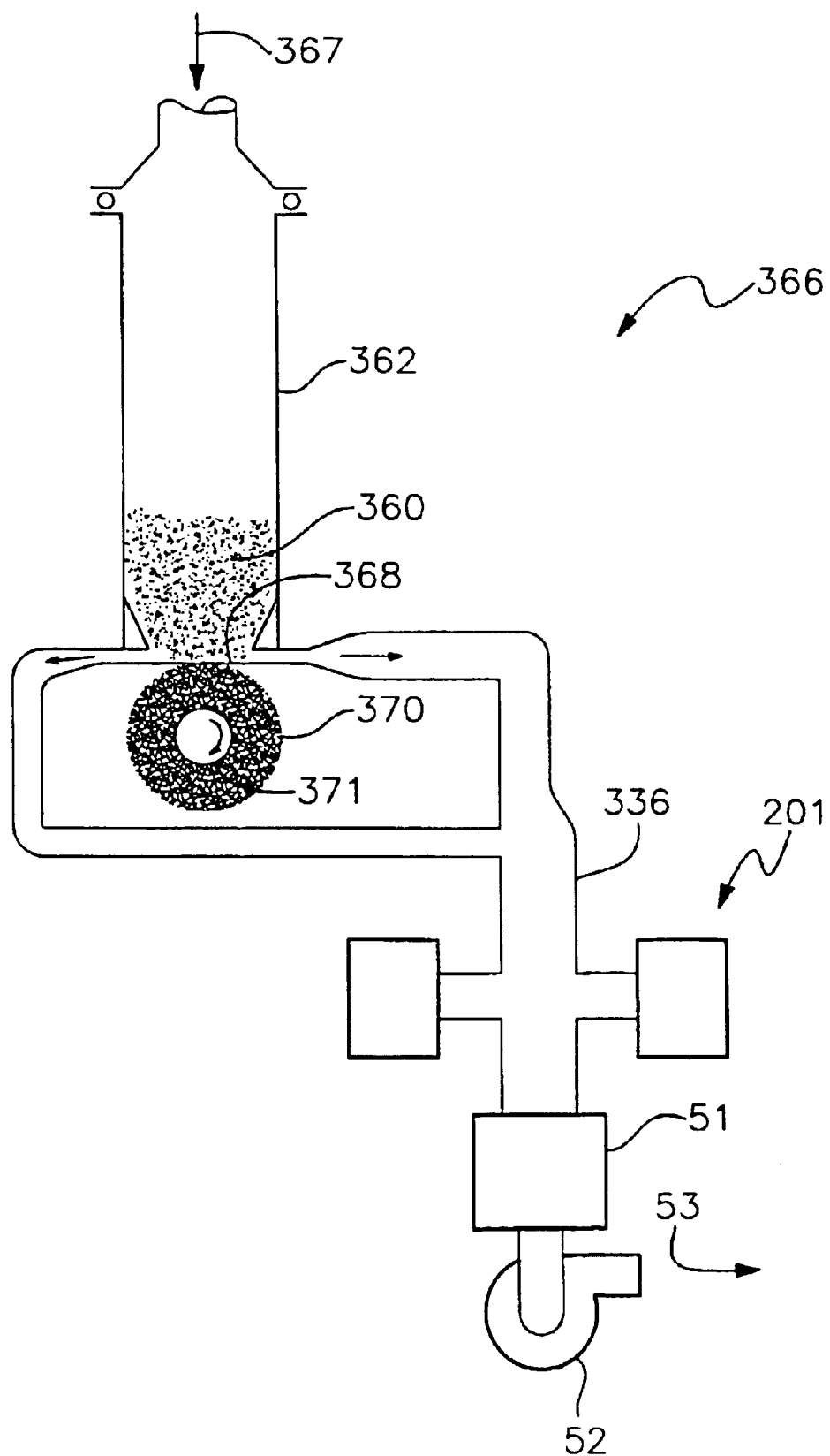
FIG. 4F is an enlarged view of a deposition section receiving the drift tube of FIG. 4E.

FIGS. 4E and 4F show another deposition embodiment for controlled aerosol delivery and deposition within a system 3, wherein aerosolized mass 360 is delivered from aerosol generator 105 as in FIG. 4B to drift tube 362. The mass amount is determined precisely and accurately according to the methods disclosed by Equation (5) and the apparatus and procedural stops thereto related, including CCM 400 as seen in FIG. 1 and understood to be controlling delivered mass amount 360 in FIG. 4E. Downstream mass concentration sensor 201 is unnecessary in this case but may be used to monitor proper operation.

After loading predetermined aerosolized mass 360, drift tube 362 is removed from the mass delivery section 365 and the next drift tube 363 is moved into position by an automatic mechanical handler (not shown). After removal from deposition section 365, drift tube 362 is inserted into deposition section 366, seen in FIG. 4F. Displacement gas 367 enters the top of drift tube 362 and, in combination with pump 52, pushes/pulls aerosol mass 360, having predetermined mass, downward and over electrostatic deposition surface 368. Downstream mass concentration sensor 201 serves the same function as in all previous deposition embodiments.

Electrostatic charges on and in plastic deposition film 368 are generated by mechanical rubbing contact of dissimilar material 370 on roller 371 with deposition film 368. Collection efficiencies of this method are satisfactory provided the velocities of the powder particles 360 approaching the deposition film are low, of order 1 cm/sec. (This velocity is in contrast to velocities of order 1 m/s for porous media of FIG. 4A or order 10 m/s for impaction of FIG. 4B.)

The loading of drift tubes 362 in FIG. 4E and deposition of the predetermined load or dose of aerosolized mass 360 are advantageously separate operations. Loading of tens of micrograms may require only five seconds in mass delivery section 365 (FIG. 4E), whereas deposition of that loan in deposition section 366 (FIG. 4F) may require 100 seconds. Thus, one loading section 365 can service about twenty deposition sections 366.

INDUSTRIAL APPLICABILITY

The way in which the invention is capable of being exploited and the way in which it can be made and used will be apparent from the foregoing.

What is claimed is:

1. A system for delivery and deposition of aerosolized masses, comprising:

an aerosol generator;

an upstream electro-optical mass concentration sensor, and a source of gas flow for transporting aerosols past said upstream electro-optical mass concentration sensor at a known upstream volumetric flow rate;

a deposition zone for collecting aerosols on or within a media;

a downstream electro-optical mass concentration sensor for measuring the mass concentration of aerosols uncollected in said deposition zone, and a conduit for transporting uncollected aerosols past said downstream electro-optical mass concentration sensor at a known downstream volumetric flow rate; and a controller connected to said upstream and downstream mass concentration sensors and determining the net mass of aerosols collected within said deposition zone by integrating over time the product of mass concentration measured by said upstream electro-optical sensor and the known upstream volumetric flow rate minus the product of mass concentration measured by said downstream electro-optical sensor and the known downstream volumetric flow rate.

2. The system of claim 1, which further comprises an upstream volumetric flow rate sensor for determining the upstream volumetric flow rate, and wherein said controller is connected to said upstream volumetric flow rate sensor.

3. The system of claim 2, which further comprises a downstream volumetric flow rate sensor for determining the downstream volumetric flow rate, and wherein said controller is connected to said downstream volumetric flow rate sensor.

4. The system of claim 1, wherein said aerosol generator comprises:

a metering pocket, with powder loaded into said metering pocket;

a jet for directing high velocity gas into said metering pocket so as to fluidize the powder and produce an expansive bolus; and a mixing chamber into which the expansive bolus is directed.

5. The system of claim 4, wherein said metering pocket is a micropocket having a volume of the order of one cubic millimeter.

6. The system claim 5, wherein said aerosol generator further comprises:

a powder chamber containing powder to be aerosolized;

a sealing gland separating said powder chamber and said mixing chamber; and wherein said micropocket metering pocket comprises a microscoop in the form of a plunger rod having a tip with said micropocket metering pocket formed within said tip, said plunger rod passing through powder in said powder chamber so as to load powder within said micropocket metering pocket and then engaging and penetrating said sealing gland.

7. The system of claim 5, wherein said aerosol generator, further comprises:

a body;

a powder pocket cylinder cavity within said body and a powder pocket cylinder within said powder pocket cylinder cavity, said powder pocket cylinder having an outer cylindrical surface and a plurality of metering pockets formed within said cylindrical surface, and a passageway within said body communicating with a metering pocket of said plurality when said metering pocket is in an active position so as to provide access to said metering pocket.

8. The system of claim 7, wherein said aerosol generator further comprises:
a metering cylinder cavity within said body and a rotating metering cylinder within said metering cylinder cavity, said rotating metering cylinder comprising an outer tube with first and second openings in the wall of said outer tube, said first opening being selectively alignable with said passageway communicating with said metering pocket; and wherein
said gas jet is within said outer tube and directs high velocity gas through said first opening into said metering pocket, thereby fluidizing powder which passes through said first opening into the interior of said outer tube and out through said second opening as an expansive bolus.

9. The system of claim 5, wherein said aerosol generator further comprises a megadose disc having a surface and a plurality of metering pockets formed in said surface.

10. The system of claim 4, wherein said jet directs gas at a velocity approaching Mach 1 into said metering pocket.

11. The system of claim 1, wherein said aerosol generator comprises:
a source of a liquid solution of an active ingredient and a volatile solvent;
an atomizer for atomizing the solution to produce droplets from which the solvent evaporates to leave an expansive bolus of solute residue; and
a mixing chamber into which the expansive bolus is directed.

12. The system of claim 1, wherein said deposition zone comprises:
a porous media collection element;
an aerosol delivery tube positioned generally against an upstream side of said porous media collection element for delivering aerosols transported by a fluid; and
a perforated support element positioned generally against a downstream side of said porous media collection element.

13. The system of claim 1 wherein said deposition zone comprises:
an impactor plate;
an impactor jet for directing aerosols transported by a fluid against said impactor plate for deposition thereon; and
an output conduit for conveying away fluid and aerosols not deposited on said impactor plate.

14. The system of claim 13, wherein said impactor jet directs aerosols transposed by a gas at a velocity approaching Mach 1 against said impactor plate.

15. The system of claim 1 wherein said deposition zone comprises:
a mass delivery section for loading an aerosolized mass into a removable drift tube; and
a deposition section receiving said drift tube and including a source of displacement gas for directing the aerosolized mass over a deposition surface.

16. The system of claim 15, wherein said deposition surface is electrostatically charged for attracting aerosols.

17. An aerosol generator for producing an aerosolized powder, said aerosol generator comprising:
a metering pocket having a volume of the order of one cubic millimeter, with powder loaded into said metering pocket;
a powder chamber containing powder to be aerosolized a mixing chamber;
a sealing gland separating said powder chamber and said mixing chamber;
said micropocket metering pocket comprising a microscoop in the form of a plunger rod having a tip with said micropocket metering pocket formed within said tip, said plunger rod passing through powder in said powder chamber so as to load powder within said micropocket metering pocket and then engaging and penetrating said sealing gland;
a jet for directing high velocity gas into said metering pocket, soas to fluidize the powder and produce an expansive which is directed into said mixing chamber.

18. A deposition zone for collecting aerosolized masses, comprising:
a porous media collection element;
an aerosol delivery tube positioned generally against an upstream side of said porous media collection element for delivering aerosols transported by a fluid, said aerosol delivery tube having a tapered end;
a perforated support element positioned generally against a downstream side of said porous media collection element, said perforated support element being cup-like in configuration with a tapered interior surface; and
said porous media collection element being cup-like in configuration having a tapered interior surface matching the tapered end of said aerosol delivery tube as the upstream side, and a tapered exterior surface matching the taper of said perforated support element as the downstream side.

19. A system for delivery and deposition of aerosolized masses, comprising:
an aerosol generator;
an upstream electro-optical mass concentration sensor, and a source of gas flow for transporting aerosols past said upstream electro-optical mass concentration sensor at a known upstream volumetric flow rate;
a deposition zone for collecting aerosols on or within a media;
a controller connected to said upstream mass concentration sensor and determining the mass of aerosols delivered to said deposition zone by integrating over time the product of mass concentration measured by said upstream electro-optical sensor and the known upstream volumetric flow rate.

20. A system for delivery and deposition of aerosolized masses, comprising:
an aerosol generator;
a source of gas flow for transporting aerosols;
a deposition zone for collecting aerosols on or within a media;
a downstream electro-optical mass concentration sensor for measuring the mass concentration of aerosols uncollected in said deposition zone, and a conduit for transporting uncollected aerosols past said downstream electro-optical mass concentration sensor at a known downstream volumetric flow rate; and
a controller connected to said downstream mass concentration sensor and determining the mass of aerosols not collected within said deposition zone by integrating over time the product of mass concentration measured by said downstream electro-optical sensor and the known downstream volumetric flow rate.

* * * * *